United States Patent [19]

Coates et al.

[11] Patent Number: 5,205,962

[45] Date of Patent: Apr. 27, 1993

[54] PYRIDINE DERIVATIVES

[75] Inventors: David Coates, Dorset; Simon Greenfield, Poole; Ian C. Sage, Broadstone; Robert Clemitson, Poole, all of Great Britain; Herbert Plach, Darmstadt; Volker Reiffenrath, Rossdorf, both of Fed. Rep. of Germany

[73] Assignee: Merck Patent Gesellschaft Mit Beschrankter Haftung, Fed. Rep. of Germany

[21] Appl. No.: 651,392

[22] PCT Filed: Sep. 12, 1990

[86] PCT No.: PCT/EP90/01536

§ 371 Date: Feb. 6, 1991

§ 102(e) Date: Feb. 6, 1991

[87] PCT Pub. No.: WO91/04248

PCT Pub. Date: Apr. 4, 1991

[30] Foreign Application Priority Data

Sep. 22, 1989 [GB] United Kingdom ............... 8921520

[51] Int. Cl.$^5$ .................. C09K 19/34; C07D 213/54; C07D 213/61; C07D 239/02
[52] U.S. Cl. ......................... 252/299.61; 252/299.01; 544/242; 544/325; 546/290; 546/303; 546/339; 546/345; 359/103
[58] Field of Search ...................... 252/299.01, 299.61; 546/290, 303, 329, 339, 345; 544/202, 335; 359/103

[56] References Cited

U.S. PATENT DOCUMENTS 4,684,477 8/1987 Sugimori et al. ............. 252/299.61

FOREIGN PATENT DOCUMENTS 0310676 12/1987 European Pat. Off. .

Primary Examiner—Robert L. Stoll
Assistant Examiner—Shean C. Wu
Attorney, Agent, or Firm—Millen, White, Zelano & Branigan

[57] ABSTRACT

The invention relates to pyridine derivatives of the formula I

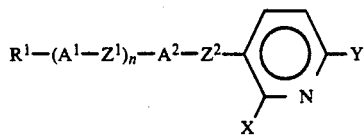

wherein $R^1$, $A^1$, $E^1$, n, $A^2$, $Z^2$, X and Y have the meaning given in claim 1.

15 Claims, No Drawings

PYRIDINE DERIVATIVES

SUMMARY OF THE INVENTION

The invention relates to pyridine derivatives of the formula I

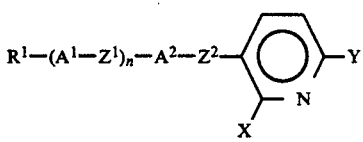

wherein
R$^1$ denotes alkyl with up to 12 carbon atoms wherein one or two non-adjacent CH$_2$-groups may also be replaced by —O—, —O—CO—, —CO—O— and/or —CH=CH—,
Y is F, Cl, —CF$_3$, —OCF$_3$ or —OCF$_2$H,
A$^1$ and A$^2$ in each case independently of one another are trans-1,4-cyclohexylene, wherein one or two non-adjacent CH$_2$-groups may also be replaced by —O— and/or —S—, or 1,4-phenylene which is unsubstituted or substituted by one or more halogen atoms and/or nitrile and/or CH$_3$ groups, and wherein one or more CH groups may also be replaced by N,
Z$^1$ and Z$^2$ in each case independently of one another are —CH$_2$CH$_2$—, —CO—O—, —O—CO—, —CH$_2$O—, —OCH$_2$—, —C≡C— or a single bond,
X is H, or in case of Y=F or Cl, also F and
n is 0, 1 or 2,
and also to liquid crystalline media being a mixture of at least 2 compounds, characterized in that at least one compound is a pyridine derivative according to formula I.

The invention was based on the object of discovering new stable liquid crystal or mesogenic compounds which are suitable as components of liquid crystalline media and, in particular have advantageous values of optical and dielectric anisotropy, in particular for the value of Δε/ε⊥, combined with high nematogenity.

Similar pyridine compounds with cyano as the terminal group instead of fluoro or chloro atoms or —CF$_3$ groups are, for example, described in EP 0194153.

It has now been found that pyridine derivatives of the formula I are highly suitable as components of liquid crystalline media. In particular, they have advantageous values of optical and dielectric anisotropy and especially advantageous low values of Δε/ε⊥. A small ratio of Δε/ε⊥ has an important influence on the electrooptic characteristics of TN liquid crystal cells.

It is also possible to obtain stable liquid crystal phases with a broad nematic mesophase range including a good deep temperature behaviour and a comparatively low viscosity with the aid of these compounds.

Depending on the choice of the substituents, the compounds of the formula I can be used as the base materials from which liquid crystal media are predominantly composed; however, it is also possible for compounds of the formula I to be added to liquid crystal base materials of other classes of compounds, for example in order to influence the dielectric and/or optical anisotropy and/or the viscosity and/or the nematic mesophase range of such a dielectric.

The compounds of the formula I are colourless in the pure state and are liquid crystalline in a temperature range which is favourable placed for electrooptical use. They are very stable towards chemicals, heat and light.

The compounds of the formula I are further highly useful as starting material for the preparation of liquid crystalline compounds having the structural element

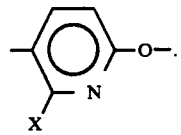

The invention thus relates to the pyridine derivatives of the formula I, to liquid crystalline media with at least two liquid crystalline compounds, wherein at least one component is a compound of the formula I and to liquid crystal display devices containing such media.

Above and below R$^1$, Y, A$^1$, A$^2$, Z$^1$, Z$^2$, n and X have the meaning indicated, unless something else is specifically stated.

For the sake of simplicity in the following, Phe is a 1,4-phenylene group which may be substituted by one or more halogen atoms and/or CN and/or CH$_3$ groups, Cyc is a trans-1,4-cyclohexylene group, Dio is a 1,3-dioxane-2,5-diyl group, Dit is a 1,3-dithian-2,5-diyl group, Pyd is a pyridine-2,5-diyl group and Pyr is a pyrimidine-2,5-diyl group. PydX denotes the group

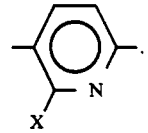

The compounds of the formula I accordingly also include compounds of the partial formulae Ia to Ib (having two rings), Ic to If (having three rings) and Ig to In (having four rings):

| | |
|---|---|
| R$^1$—A$^2$—PydX—Y | Ia |
| R$^1$—A$^2$—Z$^2$—PydX—Y | Ib |
| R$^1$—A$^1$—A$^2$—PydX—Y | Ic |
| R$^1$—A$^1$—A$^2$—Z$^2$—PydX—Y | Id |
| R$^1$—A$^1$—Z$^1$—A$^2$—PydX—Y | Ie |
| R$^1$—A$^1$—Z$^1$—A$^2$—Z$^2$—PydX—Y | If |
| R$^1$—A$^1$—A$^1$—A$^2$—PydX—Y | Ig |
| R$^1$—A$^1$—Z$^1$—A$^1$—A$^2$—PydX—Y | Ih |
| R$^1$—A$^1$—A$^1$—Z$^1$—A$^2$—PydX—Y | Ii |
| R$^1$—A$^1$—A$^1$—A$^2$—Z$^2$—PydX—Y | Ij |
| R$^1$—A$^1$—Z$^1$—A$^1$—Z$^1$—A$^2$—PydX—Y | Ik |
| R$^1$—A$^1$—Z$^1$—A$^1$—A$^2$—Z$^2$—PydX—Y | Il |
| R$^1$—A$^1$—A$^1$—Z$^1$—A$^2$—Z$^2$—PydX—Y | Im |
| R$^1$—A$^1$—Z$^1$—A$^1$—Z$^1$—A$^2$—Z$^2$—PydX—Y | In |

Among these, those of the formulae Ia, Ib, Ic, Id, Ie, Ih, Ii, Ik and Il are particularly preferred.

The preferred compounds of the partial formulae Ia include those of the partial formulae Iaa to Iad:

| | |
|---|---|
| R$^1$—Phe—PydX—Y | Iaa |
| R$^1$—Cyc—PydX—Y | Iab |
| R$^1$—Pyd—PydX—Y | Iac |
| R$^1$—Pyr—PydX—Y | Iad |

Among these, those of the formulae Iaa and Iab are particularly preferred.

The preferred compounds of the partial formula Ib include those of the partial formulae Iba to Ibj:

| | |
|---|---|
| $R^1$—Phe—C≡C—PydX—Y | Iba |
| $R^1$—Cyc—C≡C—PydX—Y | Ibb |
| $R^1$—Phe—CO—O—PydX—Y | Ibc |
| $R^1$—Cyc—CO—O—PydX—Y | Ibd |
| $R^1$—Phe—$CH_2CH_2$—PydX—Y | Ibe |
| $R^1$—Cyc—$CH_2CH_2$—PydX—Y | Ibf |
| $R^1$—Phe—$CH_2O$—PydX—Y | Ibg |
| $R^1$—Cyc—$CH_2O$—PydX—Y | Ibh |
| $R^1$—Pyd—$Z^2$—PydX—Y | Ibi |
| $R^1$—Pyr—$Z^2$—PydX—Y | Ibj |

Among these, those of the formulae Iba, Ibb, Ibc, Ibd and Ibe are particularly preferred.

The preferred compounds of the partial formula Ic include those of the partial formulae Ica to Ich:

| | |
|---|---|
| $R^1$—Cyc—Cyc—PydX—Y | Ica |
| $R^1$—Phe—Phe—PydX—Y | Icb |
| $R^1$—Dio—Phe—PydX—Y | Icc |
| $R^1$—Dit—Phe—PydX—Y | Icd |
| $R^1$—Cyc—Phe—PydX—Y | Ice |
| $R^1$—Pyd—Phe—PydX—Y | Icf |
| $R^1$—Phe—Pyr—PydX—Y | Icg |
| $R^1$—Phe—Cyc—PydX—Y | Ich |

Among these, those of the partial formulae Ica, Icb, Ice and Icf are particularly preferred.

The preferred compounds of the partial formula Id include those of the partial formulae Ida to Idm:

| | |
|---|---|
| $R^1$—Cyc—Cyc—C≡C—PydX—Y | Ida |
| $R^1$—Phe—Phe—C≡C—PydX—Y | Idb |
| $R^1$—Cyc—Phe—C≡C—PydX—Y | Idc |
| $R^1$—Cyc—Phe—$CH_2CH_2$—PydX—Y | Idd |
| $R^1$—Cyc—Cyc—$CH_2CH_2$—PydX—Y | Ide |
| $R^1$—Phe—Phe—$CH_2CH_2$—PydX—Y | Idf |
| $R^1$—Cyc—Cyc—COO—PydX—Y | Idg |
| $R^1$—Phe—Cyc—COO—PydX—Y | Idh |
| $R^1$—Phe—Phe—COO—PydX—Y | Idi |
| $R^1$—Cyc—Phe—COO—PydX—Y | Idj |
| $R^1$—Phe—Phe—$CH_2O$—PydX—Y | Idk |
| $R^1$—Cyc—Phe—$CH_2O$—PydX—Y | Idl |
| $R^1$—Cyc—Cyc—$CH_2O$—PydX—Y | Idm |

Among these, those of the formulae Ida, Idb, Idc, Ide, Idg and Idh are particularly preferred.

The preferred compounds of the partial formula Ie include those of the partial formulae Iea to Iem:

| | |
|---|---|
| $R^1$—Cyc—$CH_2CH_2$—Phe—PydX—Y | Iea |
| $R^1$—Phe—$CH_2CH_2$—Phe—PydX—Y | Ieb |
| $R^1$—Cyc—C≡C—Phe—PydX—Y | Iec |
| $R^1$—Phe—C≡C—Phe—PydX—Y | Ied |
| $R^1$—Phe—$CH_2O$—Phe—PydX—Y | Iee |
| $R^1$—Cyc—COO—Phe—PydX—Y | Ief |
| $R^1$—Cyc—COO—Cyc—PydX—Y | Ieg |
| $R^1$—$A^1$—OCO—Phe—PydX—Y | Ieh |
| $R^1$—$A^1$—$OCH_2$—Phe—PydX—Y | Iei |
| $R^1$—$A^1$—$Z^1$—Pyd—PydX—Y | Iej |
| $R^1$—$A^1$—$Z^1$—Pyr—PyrdX—Y | Iek |
| $R^1$—Cyc—C≡C—Cyc—PydX—Y | Iel |
| $R^1$—Cyc—$CH_2CH_2$—Cyc—PydX—Y | Iem |

Among these, those of partial formulae Iea, Ieb, Iec, Ied, Ieg and Iel are particularly preferred.

The preferred compounds of the partial formula If include those of the partial formulae Ifa to Ifh:

| | |
|---|---|
| $R^1$—$A^1$—$Z^1$—Phe—C≡C—PydX—Y | Ifa |
| $R^1$—$A^1$—$CH_2CH_2$—Phe—$CH_2CH_2$—PydX—Y | Ifb |
| $R^1$—$A^1$—$Z^1$—Phe—$CH_2CH_2$—PydX—Y | Ifc |
| $R^1$—$A^1$—$Z^1$—Cyc—COO—PydX—Y | Ifd |
| $R^1$—Cyc—$Z^1$—Cyc—C≡C—PydX—Y | Ife |
| $R^1$—Cyc—$Z^1$—Cyc—$CH_2CH_2$—PydX—Y | Iff |
| $R^1$—$A^1$—COO—Phe—$Z^2$—PydX—Y | Ifg |
| $R^1$—$A^1$—$CH_2O$—Phe—$Z^2$PydX—Y | Ifh |

The preferred compounds of the formulae Ig to In include those of the partial formulae Iga to Igo:

| | |
|---|---|
| $R^1$—$A^1$—Cyc—Cyc—PydX—Y | Iga |
| $R^1$—Cyc—Cyc—Phe—PydX—Y | Igb |
| $R^1$—Phe—Phe—Cyc—PydX—Y | Igc |
| $R^1$—$A^1$—$CH_2CH_2$—$A^1$—Cyc—PydX—Y | Igd |
| $R^1$—Cyc—COO—$A^1$—Phe—PydX—Y | Ige |
| $R^1$—$A^1$—$A^1$—$CH_2CH_2$—Phe—PydX—Y | Igf |
| $R^1$—Cyc—Cyc—$Z^1$—$A^2$—PydX—Y | Igg |
| $R^1$—$A^1$—Phe—Phe—C≡C—PydX—Y | Igh |
| $R^1$—$A^1$—Cyc—Phe—C≡C—PydX—Y | Igi |
| $R^1$—$A^1$—$A^1$—$A^2$—$CH_2CH_2$—PydX—Y | Igj |
| $R^1$—$A^1$—$A^1$—$A^2$—COO—PydX—Y | Igk |
| $R^1$—Cyc—COO—$A^1$—$Z^1$—Phe—PydX—Y | Igl |
| $R^1$—Phe—C≡C—$A^1$—$Z^1$—Phe—PydX—Y | Igm |
| $R^1$—$A^1$—$CH_2CH_2$—Cyc—Cyc—$CH_2CH_2$—PydX—Y | Ign |
| $R^1$—$A^1$—$Z^1$—Phe—Phe—$Z^2$—PydX—Y | Igo |

In the compounds of the formulae above and below Y is F, Cl, —$CF_3$, —O $CF_3$ or —$OCF_2H$, preferably F or —$CF_3$. X is H or F, preferably H. However, in case of Y is F or Cl, X preferably is F, too.

In the compounds of the formulae above and below $R^1$ is preferably alkyl, alkoxy, oxaalkyl, alkanoyloxy or alkenyl and can exhibit a straight-chain or branched structure.

Alkyl or alkoxy preferably are straight-chain and have 2, 3, 4, 5, 6 or 7 C atoms. Accordingly they are preferably ethyl, propyl, butyl, pentyl, hexyl, heptyl, ethoxy, propoxy, butoxy, pentoxy, hexoxy, or heptoxy, also methyl, octyl, nonyl, decyl, undecyl, dodecyl, methoxy, octoxy, nonoxy, decoxy or undecoxy Oxaalkyl is preferably straight-chain 2-oxapropyl (=methoxymethyl), 2-(=ethoxymethyl) or 3-oxybutyl (=2-methoxyethyl), 2-, 3- or 4-oxapentyl, 2-, 3-, 4- or 5-oxahexyl, 2-, 3-, 4- 5- or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8-, or 9-oxadecyl.

Alkenyl is preferably straight-chain and has 2 to 10 C atoms. It is accordingly, in particular, vinyl, prop-1- or prop-2-enyl, but-1-, -2- or -3-enyl, pent-1-, -2-, -3- or -4-enyl, hex-1-, -2-, -3-, -4- or TM 5-enyl, hept-1-, -2-, -3-, -4-, -5- or -6-enyl, oct-1-, -2-, -3-, -4-, -5- -6- or -7-enyl, non-1-, -2-, -3-, -4-, -5-, -6-, -7- or -B-enyl or dec-1-, -2-, -3-, -4-, -5-, -6-, -7-, -8- or -9-enyl.

Compounds of the formula I containing a branched terminal group can occasionally be of importance because of an improved solubility in the customary liquid crystal base materials, but in particular as chiral doping substances if they are optically active.

Branched groups of this type as a rule contain not more than one chain branching. Preferred branched radicals are isopropyl, 2-butyl (=1-methylpropyl), isobutyl (=2-methylpropyl, 2-methylbutyl, isopentyl, (=3-methylbutyl), 2-methylpentyl, 2-ethylhexyl, 2-propylpentyl, 2-octyl, isopropoxy, 2-methylpropoxy, 2-methylbutoxy, 3-methylbutoxy, 2-methylpentoxy, 3-methylpentoxy, 2-ethylhexoxy, 2-methylhexoxy, 1-methylhexoxy, 1-methylheptoxy (=2-octyloxy), 2-oxa- 3-methylbutyl, 3-oxa-4-methylhexyl, 2-nonyl, 2-decyl, 2-dodecyl, 6-methyloctoxy, 6-methyloctanoyloxy, 4-methylheptyloxycarbonyl, 2-methylbutyryloxy, 3-methylvaleryloxy, 4-methylhexanoyloxy, 2-methyl-3-oxapentyl and 2-methyl-3-oxahexyl.

In the case of compounds with a branched terminal group R¹, formula I includes both the optical antipodes and racemates as well as mixtures thereof.

n is preferably 0 or 1. If n is 2, the two groups A¹ and Z¹ may be identical or different from one another.

Z¹ and Z² are preferably a single bond, a —CH₂CH₂—, a —CO—O— or a —CH₂CH₂-group, also —O—CO—, —CH₂O— or —OCH₂—.

A¹ and A² are preferably unsubstituted 1,4-phenylene or trans 1,4-cyclohexylene. Compounds wherein A and-/or A² are substituted 1,4-phenylene are also preferred. They are then preferably mono- or disubstituted by fluorine and the 1,4-phenylene group has preferably the following structures:

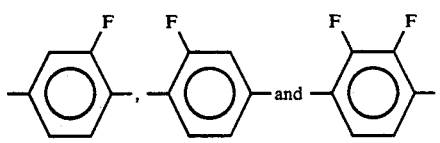

A¹ and A² also preferably have the meaning of Pyd or Pyr.

the following group of compounds of the formula I is particularly preferred:

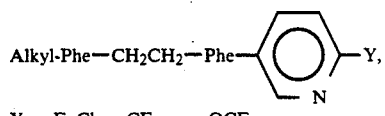

Y = F, Cl, —CF₃ or —OCF₃

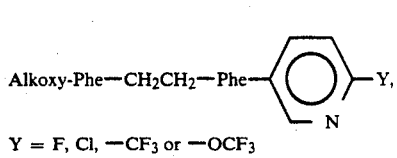

Y = F, Cl, —CF₃ or —OCF₃

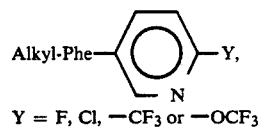

Y = F, Cl, —CF₃ or —OCF₃

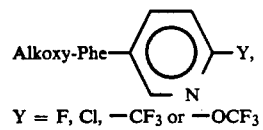

Y = F, Cl, —CF₃ or —OCF₃

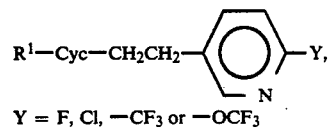

Y = F, Cl, —CF₃ or —OCF₃

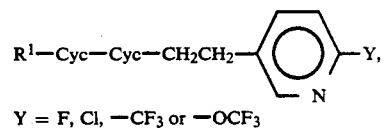

Y = F, Cl, —CF₃ or —OCF₃

-continued

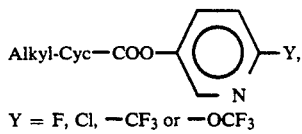

Y = F, Cl, —CF₃ or —OCF₃

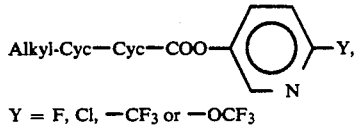

Y = F, Cl, —CF₃ or —OCF₃

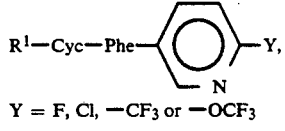

Y = F, Cl, —CF₃ or —OCF₃

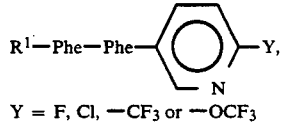

Y = F, Cl, —CF₃ or —OCF₃

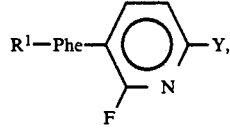

Y = F or Cl

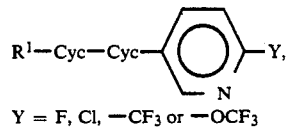

Y = F, Cl, —CF₃ or —OCF₃

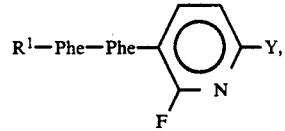

Y = F or Cl

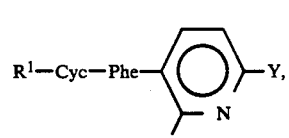

Y = F or Cl

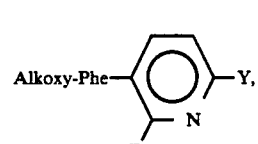

Y = F or Cl

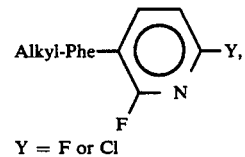

Y = F or Cl

-continued

Alkyl-Cyc—COO—[Pyridine]—Y, (F at 3-position, N)
Y = F or Cl

Alkyl-Cyc—Cyc—COO—[Pyridine]—Y, (F at 3-position, N)
Y = F or Cl

R¹—Phe—C≡C—[Pyridine-X]—Y,
Y = F, Cl or —CF₃

R¹—Cyc—Cyc—[Pyridine]—Y, (F at 3-position)
Y = F or Cl

R¹—Cyc—Phe—[Pyridine-X]—Y,
Y = F, Cl, —CF₃ or —OCF₃

R¹—[Pyridine-N]—[Pyridine-X-N]—Y,
Y = F, Cl, —CF₃ or —OCF₃

R¹—[Pyridine-N,N]—[Pyridine-X-N]—Y,
Y = F, Cl, CF₃ or —OCF₃

R¹—Cyc—CH₂CH₂—Phe—[Pyridine-X]—Y,
Y = F or Cl

R¹—Phe—CH₂CH₂—Phe—[Pyridine-X]—Y,
Y = F or Cl

-continued

R¹—Phe—Phe—C≡C—[Pyridine-X]—Y,
Y = F, Cl, —CF₃ or —OCF₃

R¹—Cyc—Cyc—C≡C—[Pyridine-X]—Y,
Y = F, Cl, —CF₃ or —OCF₃

R¹—Cyc—Phe—C≡C—[Pyridine-X]—Y,
Y = F, Cl, —CF₃ or —OCF₃

R¹—Cyc—Phe—CH₂CH₂—[Pyridine-X]—Y,
Y = F, Cl, —CF₃ or —OCF₃

R¹—Phe—Phe—CH₂CH₂—[Pyridine-X]—Y,
Y = F, Cl, —CF₃ or —OCF₃

R¹—Cyc—Cyc—CH₂—CH₂—[Pyridine-X]—Y,
Y = F or Cl

Of The compounds of the formula I and subformula thereof, those in which at least one of the radicals contained therein has one of the preferred meanings given are preferred.

The compounds of the formula I are prepared by methods which are known per se, such as are described in the literature (for example in the standard works, such as Houben-Weyl, Methoden der Organischen Chemie [Methods of Organic Chemistry, Georg Thieme Verlag, Stuttgart), and in particular under reaction conditions which are known and suitable for the reactions mentioned. Variants which are known per se and are not mentioned in more detail here can also be used in this connection.

If desired, the starting materials can also be formed in situ, such that they are not isolated from the reaction mixture but are immediately reacted further to give the compounds of the formula I.

The most important starting materials for most of the synthesis routes are the following substances:

a) 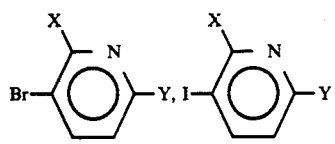
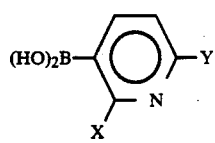
c) 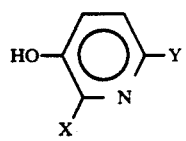
these key intermediates are preparable by the following routes (LDA=lithiumdiisopropylamide)
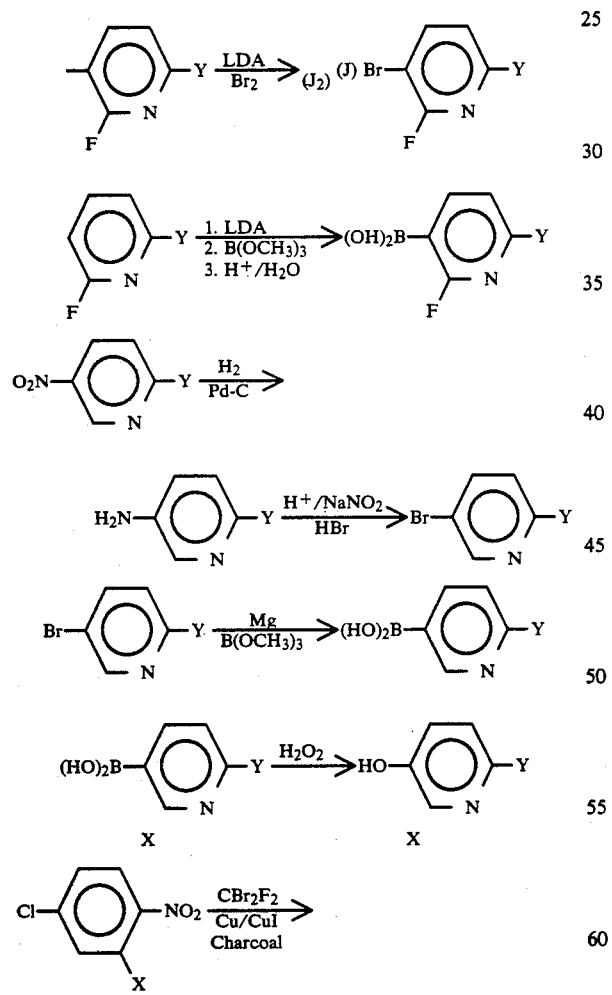
a) 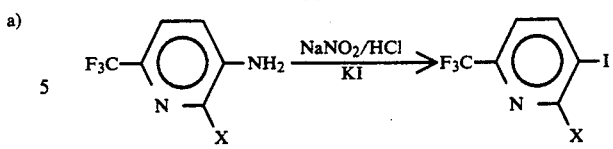
b) The compounds of the formula I thus can be prepared preferably by the following coupling reactions which are known per se:
Scheme 1
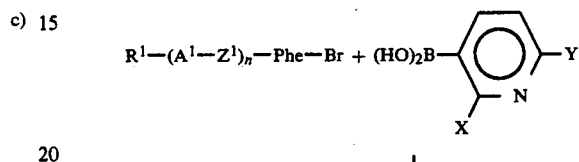
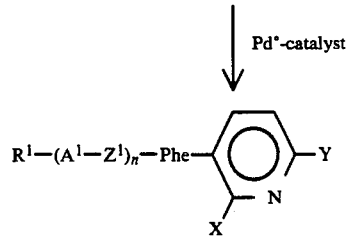
Scheme 2
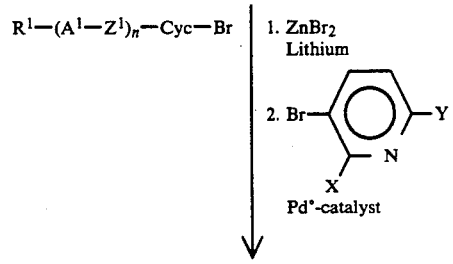
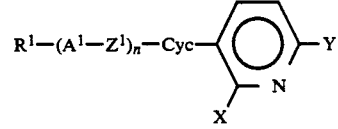
Scheme 3
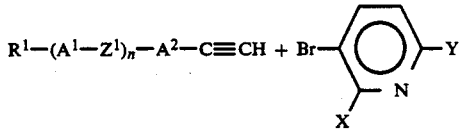
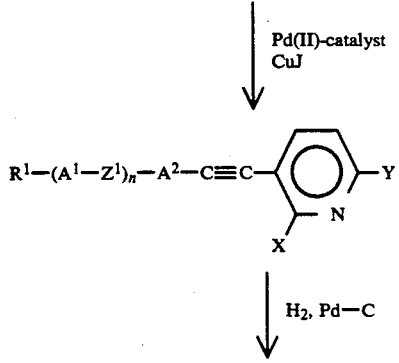

-continued

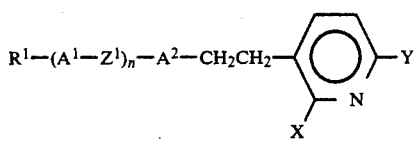

Scheme 4

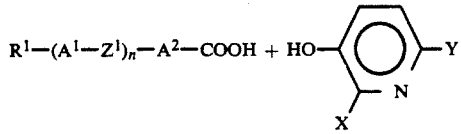

dicyclohexylcarbo-
diimide (DCC)
dimethylamino-
pyridine (DMAP)

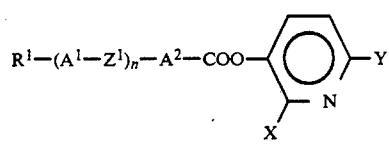

Scheme 5

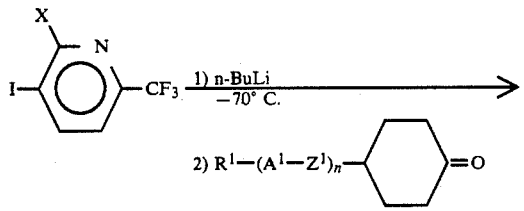

2) R¹—(A¹—Z¹)ₙ—[cyclohexanone]=O

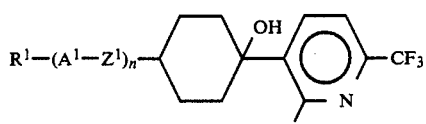

pTSA

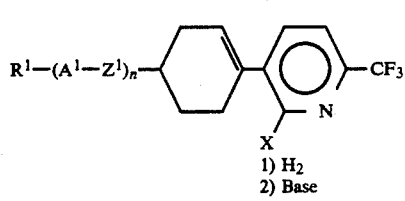

1) H₂
2) Base

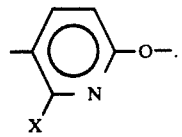

Scheme 6

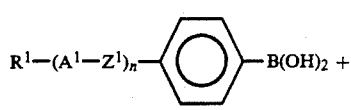

-continued

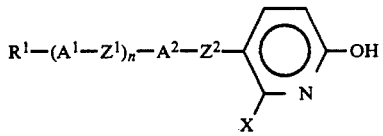

The compounds of the formula I wherein X denotes —OCF₃ can be obtained for example from the compounds of the formula I wherein X denotes Cl or F by nucleophilic substitution with sodium trifluoromethanolate.

The compounds of the formula I wherein X denotes —OCF₂H can be prepared as described in WO 90/01056, for example, by reacting the hydroxypyridines of the formula I'

$$R^1-(A^1-Z^1)_n-A^2-Z^2-\underset{X}{\underset{N}{\text{pyridine}}}-OH \quad I'$$

with chlorodifluoromethane.

The reaction conditions are known to the skilled worker or described in the literature already mentioned. Other routes are apparent to the skilled worker.

Compounds of the formula I wherein X=Y=F are highly useful as starting materials for liquid crystalline compounds with the structural element $$-\underset{X}{\underset{N}{\text{pyridine}}}-O-.$$

Compounds having this structural element are obtained by a nucleophilic substitution of the terminal F atom by —OR, wherein R is an organic residue.

In addition to one or more compounds of the formula I the liquid crystal media according to the invention preferably contain 2–40 components and in particular 4–30 components. Liquid crystal media being composed of one or more compounds of formula I and 7–25 other components are especially preferred.

These additional components are preferably chosen from the nematic or nematogenic (monotropic or isotropic) substances; in particular from the classes of azoxybenzenes, benzylideneanilines, biphenyls, terphenyls, phenyl or cyclohexyl benzoates, phenyl or cyclohexyl cyclohexanecarboxylates, phenyl or cyclohexyl cyclohexylbenzoates, phenyl or cyclohexyl cyclohexylcyclohexanecarboxylates, cyclohexylphenylbenzoates, cyclohexylphenyl cyclohexanecarboxylates, cyclohexylphenyl cyclohexylcyclohexanecarboxylates, phenylcyclohexanes, cyclohexylbiphenyls, phenylcyclohexylcyclohexanes, cyclohexylcyclohexanes, cyclohexylcyclohexenes, cyclohexylcyclohex- Ylcyclohexene, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyldioxanes, phenyl- or cyclo TM hexyl-1,3-dithianes, 1,2-diphenylethanes, 1,2-dicyclohexyle-thanes, 1-phenyl-2-cyclohexylethanes, 1-cyclohexyl-2-(4-phenyl-cyclohex-yl)-ethanes, 1-cyclohexyl-2-biphenylethanes, 1-phenyl-2-cyclohex-yl-phenylethanes, optionally halogenated stilbenes, benzyl phenyl ethers, tolanes and substituted cinnamic acids.

The 1,4-phenylene groups of these compounds may be fluorinated.

The most important compounds which are possible constituents of liquid crystal media according to the invention can be characterized by the formalae 1, 2, 3, 4 and 5:

$$R'-L-U-R''  \quad 1$$

$$R'-L-COO-U-R'' \quad 2$$

$$R'-L-OOC-U-R'' \quad 3$$

$$R'-L-CH_2CH_2-U-R'' \quad 4$$

$$R'-L-C\equiv C-U-R'' \quad 5$$

In the formulae 1, 2, 3, 4 and 5 L and U may be equal or different from each other. L and U independently from each other denote a bivalent residue selected from the group consisting of -Phe-, -Cyc-, -Phe-Phe-, -Phe-Cyc-, -Cyc-Cyc-, -Pyr-, -Dio-, -G-Phe-, -G-Cyc- and their mirror images; in this compilation of residues Phe denotes unsubstituted or fluorinated 1,4-phenylene, Cyc trans- 1,4-cyclohexylene or 1,4-cyclohexenylene, Pyr pyrimidine-2,5-diyl or pyridine-2,5-diyl, Dio 1,3-dioxane-2,5-diyl and G 2-(trans-1,4-cyclohexyl)-ethyl, pyrimidine-2,5-diyl, pyridine-2,5-diyl or 1,3-dioxane-2,5-diyl.

One of the residues L and U is preferably Cyc, Phe or Pyr. U preferably denotes Cyc, Phe or Phe-Cyc. The liquid crystal media according to the invention preferably contain one or more components selected from the compounds of formulae I, 2, 3, 4 and 5 with L and U meaning Cyc, Phe and Pyr, said liquid crystal media further containing at the same time one ore more components selected from the compounds of formulae 1, 2, 3, 4 and 5 with one of the residues L and U denoting Cyc, Phe and Pyr and the other residue being selected from the group consisting of -Phe-Phe-, -Phe-Cyc-, -Cyc-Cyc-, -G-Cyc-, said liquid crystal media containing in addition to this optionally one or more components selected from the compounds of formulae I, 2, 3, 4 and 5 with L and U being selected from the group consisting of -Phe-Cyc-, -Cyc-Cyc-, -G-Phe- and -G-Cyc.

In a preferred subgroup of the compounds of formulae 1, 2, 3, 4 and 5 (subgroup 1) R' and R'' are independently from each other alkyl, alkenyl, alkoxy, alkenoxy with up to 8 carbon atoms. R' and R'' differ from one another in most of these compounds, one of the residues usually being alkyl or alkenyl. In another preferred subgroup of the compounds of formulae 1, 2, 3, 4 and 5 (subgroup 2) R'' denotes —CN, —CF$_3$, —F, —Cl or —NCS while R' has the meaning indicated in subgroup 1 and is preferably alkyl or alkenyl. Other variants of the envisaged substituents in the compounds of formulae 1, 2, 3, 4 and 5 are also customary. Many such substances are commercially available. All these substances are obtainable by methods which are known from the literature or by analogous methods.

The liquid crystal media according to the invention preferably contain in addition to components selected from subgroup 1 also components of subgroup 2, the percentage of these components being as follows:
subgroup 1: 20 to 90%, in particular 30 to 90%
subgroup 2: 10 to 50%, in particular 10 to 50%

In these liquid crystal media the percentages of the compounds according to the invention and the compounds of subgroup 1 and 2 may add up to give 100%.

The media according to the invention preferably contain 1 to 40%, in particular 5 to 30% of the compounds according to the invention. Media containing more than 40%, in particular 45 to 90% of the compounds according to the invention are further preferred. The media contain preferably 3, 4 or 5 compounds according to the invention.

The media according to the invention are prepared in a manner which is customary per se. As a rule, the components are dissolved in one another, advantageously at elevated temperature. The liquid crystal media according to the invention can be modified by suitable additives so that they can be used in all the types of liquid crystal display devices. Such additives are known to the expert and are described in detail in the literature (H. Kelker/R. Hatz, Handbook of Liquid Crystals, Verlag Chemie, Weinheim, 1980). For example, it is possible to add pleochroic dyestuffs to prepare colored guest-host systems or substances for modifying the dielectric anisotropy, the viscosity and/or the orientation of the nematic phases.

The following examples are to be construed as merely illustrative and not limitative. m.p.=melting point, c.p.=clearing point. In the foregoing and in the following all parts and percentages are by weight and the temperatures are set forth in degrees Celsius. "Customary work-up" means that water is added, the mixture is extracted with methylene chloride, the organic phase is separated off, dried and evaporated, and the product is purified by crystallization and/or chromatography.

Further are:
C: crystalline-solid state, S: smectic phase (the index denoting the type of smectic phase), N: nematic phase, Ch: cholesteric phase, I: isotropic phase. The number being embraced by 2 of these symbols denotes the temperature of phase change.

EXAMPLES

Example 1 a) 48.5 mM of magnesium in 8 ml of THF is slowly added under dry nitrogen to a mixture of 44.1 mM of 2-fluoro-5-bromopyridine (obtainable by reacting 2-chloro-5-nitropyridine with anhydrous KF in DMF at 120°, hydrogenation of the nitro-group and transferring the NH$_2$-group with NaNO$_2$ via the diazonium salt and with HBr into the bromo-derivative) in 50 ml of THF. The Grignard reagent is refluxed for a further hour, cooled in ice and 53.4 mM of trimethylborate is added. After stirring overnight the borate ester is hydrolysed with dilute HCl, the product extracted into ether, dried and the solvent removed.

b) 35 mM of 4-(trans-4-pentylcyclohexyl)-bromobenzene, 38.5 mM of 2-fluoro-pyridine-5-bromic acid and Pd(PPh$_3$)$_4$ (4×10$^{-4}$) are refluxed overnight under nitrogen, in a mixture of toluene (45 ml), aqueous Na$_2$CO$_3$ (20 ml) and 15 ml of IMS. Customary work-up gives 2-fluoro-5-[4-(trans-4-pentylcyclohexyl)phenyl]-pyridine.

The following compounds are obtained analogously:
2-fluoro-5-[4-(trans-4-ethylcyclohexyl)phenyl]-pyridine
2-fluoro-5-[4-(trans-4-propylcyclohexyl)phenyl]-pyridine
2-fluoro-5-[4-(trans-4-butylcyclohexyl)phenyl]-pyridine
2-fluoro-5-[4-(trans-4-hexylcyclohexyl)phenyl]-pyridine
2-fluoro-5-4-(trans-4-heptylcyclohexyl)phenyl]-pyridine
2-chloro-5-[4-(trans-4-ethylcyclohexyl)phenyl]-pyridine
2-chloro-5-[4-(trans-4-propylcyclohexyl)phenyl]-pyridine, K 142 N 191.3 I visc 80 cSt
2-chloro-5-[4-(trans-4-butylcyclohexyl)phenyl]-pyridine
2-chloro-5-[4-(trans-4-pentylcyclohexyl)phenyl]-pyridine
2-chloro-5-[4-(trans-4-hexylcyclohex-yl)phenyl-pyridine
2-chloro-5-[4-(trans-4-heptylcyclohexyl)phenyl]-pyridine
2-trifluoromethyl-5-[4-(trans-4-ethylcyclohexyl)-phenyl]-pyridine
2-trifluoromethyl-5-[4-(trans-4-propylcyclohexyl)-phenyl]-pyridine
2-trifluoromethyl-5-[4-(trans-4-butylcyclohexyl)-phenyl]-pyridine
2-trifluoromethyl-5-[4-(trans-4-pentylcyclohexyl)-phenyl]-pyridine
2-trifluoromethyl-5-[4-(trans-4-hexylcyclohexyl)-phenyl]-pyridine
2-trifluoromethyl-5-[4-(trans-4-heptylcyclohexyl)phenyl-pyridine
2-fluoro-5-[4-(trans-4-ethylcyclohexylethyl)phenyl]-pyridine
2-fluoro-5-[4-(trans-4-propylcyclohexylethyl)phenyl]-pyridine
2-fluoro-5-[4-(trans-4-butylcyclohexylethyl)phenyl]-pyridine
2-fluoro-5-[4-(trans-4-pentylcyclohexylethyl)phenyl]-pyridine
2-fluoro-5-[4-(trans-4-hexylcyclohexylethyl)phenyl-pyridine
2-fluoro-5-[4-(trans-4-heptylcyclohexylethyl)phenyl]-pyridine
2-chloro-5-[4-(trans-4-ethylcyclohexylethyl)phenyl]-pyridine
2-chloro-5-[4-(trans-4-propylcyclohexylethyl)phenyl]-pyridine, K 142 N 159 I visc 83 cSt
2-chloro-5-[4-(trans-4-butylcyclohexylethyl)phenyl]-pyridine
2-chloro-5-[4-(trans-4-pentylcyclohexylethyl)phenyl]-pyridine
2-chloro-5-[4-(trans-4-hexylcyclohexylethyl)phenyl]-pyridine
2-chloro-5-[4-(trans-4-heptylcyclohexylethyl)phenyl]-pyridine
2-trifluoromethyl-5-[4-(trans-4-ethylcyclohexylethyl)-phenyl]-pyridine
2-trifluoromethyl-5-[4-(trans-4-propylcyclohexylethyl)-phenyl]-pyridine
2-trifluoromethyl-5-[4-(trans-4-butylcyclohexylethyl)-phenyl]-pyridine
2-trifluoromethyl-5-[4-(trans-4-pentylcyclohexylethyl)
2-trifluoromethyl-5-[4-(trans-4-hexylcyclohexylethyl)-phenyl]-pyridine
2-trifluoromethyl-5-[4-(trans-4-heptylcyclohexylethyl)-phenyl]-pyridine
2-fluoro-5-[4-(trans-4-ethylcyclohexyl)-2-fluoro-phenyl]-pyridine
2-fluoro-5-[4-(trans-4-propylcyclohexyl)-2-fluoro-phenyl]-pyridine
2-fluoro-5-[4-(trans-4-butylcyclohexyl)-2-fluoro-phenyl]-pyridine
2-fluoro-5-[4-(trans-4-pentylcyclohexyl)-2-fluoro-phenyl]-pyridine
2-fluoro-5-[4-(trans-4-hexylcyclohexyl)-2-fluoro-phenyl]-pyridine
2-fluoro-5-[4-(trans-4-heptylcyclohexyl)-2-fluoro-phenyl]-pyridine
2-fluoro-5-[4-(trans-4-octylcyclohexyl)-2-fluoro-phenyl]-pyridine
2-chloro-5-[4-(trans-4-ethylcyclohexyl)-3-fluoro-phenyl]-pyridine
2-chloro-5-[4-(trans-4-propylcyclohexyl)-3-fluoro-phenyl]-pyridine
2-chloro-5-4-(trans-4-butylcyclohexyl)-3-fluorophenyl]-pyridine
2-chloro-5-[4-(trans-4-pentylcyclohexyl)-3-fluoro-phenyl]-pyridine
2-chloro-5-[4-(trans-4-hexylcyclohexyl)-3-fluoro-phenyl]-pyridine
2-chloro-5-[4-(trans-4-heptylcyclohexyl)-3-fluoro-phenyl]-pyridine
2-trifluoromethyl-5-4-(trans-4-ethylcyclohexylethyl)-2-fluorophenyl]-pyridine
2-trifluoromethyl-5-[4-(trans-4-propylcyclohexylethyl)-2-fluorophenyl]-pyridine
2-trifluoromethyl-5-[4-(trans-4-butylcyclohexylethyl)-2-fluorophenyl]-pyridine
2-trifluoromethyl-5-[4-(trans-4-pentylcyclohexylethyl)-2-fluorophenyl]-pyridine
2-trifluoromethyl-5-[4-(trans-4-hexylcyclohexyl)-2-fluoro-phenyl]-pyridine
2-trifluoromethyl-5-[4-(trans-4-heptylcyclohexyl)-2-fluoro-phenyl]-pyridine
2-trifluoromethyl-5-[4-(trans-4-octylcyclohexyl)-2-fluoro-phenyl]-pyridine
2-fluoro-5-(4-ethylbiphenyl-4'-yl)-pyridine
2-fluoro-5-(4-propylbiphenyl-4'-yl)-pyridine
2-fluoro TM 5-(4-butylbiphenyl-4'-yl)-pyridine
2-fluoro-5-(4-pentylbiphenyl-4'-yl)-pyridine
2-fluoro-5-(4-hexylbiphenyl-4'-yl)-pyridine
2-fluoro-5-(4-heptylbiphenyl-4'-yl)-pyridine
2-fluoro-5-(2-fluoro-4-ethylbiphenyl-4'-yl)-pyridine
2-fluoro-5-(2-fluoro-4-propylbiphenyl-4'-yl)-pyridine
2-fluoro-5-(2-fluoro-4-butylbiphenyl-4'-yl)-pyridine
2-fluoro-5-(2-fluoro-4-pentylbiphenyl-4'-yl)-pyridine
2-fluoro-5-(2-fluoro-4-hexylbiphenyl-4'-yl)-pyridine
2-fluoro-5-(2-fluoro-4-heptylbiphenyl-4'-yl)-pyridine
2-chloro-5-(2'-fluoro-4-ethylbiphenyl-4'-yl)-pyridine
2-chloro-5-(2'-fluoro-4-propylbiphenyl-4'-yl)-pyridine
2-chloro-5-(2'-fluoro-4-butylbiphenyl-4'-yl)-pyridine
2-chloro-5-(2'-fluoro-4-pentylbiphenyl-4'-yl)-pyridine
2-chloro-5-(2'-fluoro-4-hexylbiphenyl-4'-yl)-pyridine
2-chloro-5-(2'-fluoro-4-heptylbiphenyl-4'-yl)-pyridine
2-trifluoromethyl-5-(3-fluoro-4-ethylbiphenyl-4'-yl)-pyridine
2-trifluoromethyl-5-(3-fluoro-4-propylbiphenyl-4'-yl)-pyridine
2-trifluoromethyl-5-(3-fluoro-4-butylbiphenyl-4'-yl)pyridine
2-trifluoromethyl-5-(3-fluoro-4-pentylbiphenyl-4'-yl)-pyridine 2-trifluoromethyl-5-(3-fluoro-4-hexylbiphenyl-4'-yl)-pyridine
2-trifluoromethyl-5-(3-fluoro-4-heptylbiphenyl-4'-yl)-pyridine
2-trifluoromethyl-5-(3-fluoro-4-methylbiphenyl-4'-yl)-pyridine
2-trifluoromethyl-5-(4-ethoxybiphenyl-4'-yl)-pyridine
2-trifluoromethyl-5-(4-propoxybiphenyl-4'-yl)-pyridine
2-trifluoromethyl-5-(4-methoxybiphenyl-4'-yl)-pyridine
2-trifluoromethyl-5-(4-butoxybiphenyl-4'-yl)-pyridine
2-trifluoromethyl TM 5-(4-pentyloxybiphenyl-4'-yl)-pyridine
2-trifluoromethyl-5-(4-hexyloxybiphenyl-4'-yl)-pyridine
2-trifluoromethyl-5-(4-heptyloxybiphenyl-4'-yl)-pyridine
2-trifluoromethyl-5-(4-octyloxybiphenyl-4'-yl)-pyridine
2-fluoro-5-(4-ethoxybiphenyl-4'-yl)-pyridine
2-fluoro-5-(4-propoxybiphenyl-4'-yl)-pyridine
2-fluoro-5-(4-butoxybiphenyl-4'-yl)-pyridine
2-fluoro-5-(4-pentyloxybiphenyl-4'-yl)-pyridine
2-fluoro-5-(4-heptyloxybiphenyl-4'-yl)-pyridine
2-fluoro-5-(4-ethylphenyl)-pyridine
2-fluoro-5-(4-propylphenyl)-pyridine
2-fluoro-5-(4-butylphenyl)-pyridine
2-fluoro-5-(4-pentylphenyl)-pyridine
2-fluoro-5-(4-hexylphenyl)-pyridine
2-fluoro-5-(4-heptylphenyl)-pyridine
2-fluoro-5-(4-ethoxyphenyl)-pyridine
2-fluoro-5-(4-butoxyphenyl)-pyridine
2-fluoro-5-(4-propoxyphenyl)-pyridine
2-fluoro-5-(4-pentyloxyphenyl)-pyridine
2-chloro-5-(4-ethylphenyl)-pyridine
2-chloro-5-(4-propylphenyl)-pyridine
2-chloro-5-(4-butylphenyl)-pyridine
2-chloro-5-(4-pentylphenyl)-pyridine
2-chloro-5-(4-hexylphenyl)-pyridine
2-chloro-5-(4-heptylphenyl)-pyridine
2-chloro-5-(4-ethoxyphenyl)-pyridine
2-chloro-5-(4-propoxyphenyl)-pyridine
2-chloro-5-(4-pentyloxyphenyl)-pyridine
2-chloro-5-(4-octyloxyphenyl)-pyridine
2-fluoro-5-(2-fluoro-4-ethylphenyl)-pyridine
2-fluoro-5-(2-fluoro-4-propylphenyl)-pyridine
2-fluoro-5-(2-fluoro-4butylphenyl)-pyridine
2-fluoro-5-(2-fluoro-4-pentylphenyl)-pyridine
2-fluoro-5-(2-fluoro-4-hexylphenyl)-pyridine
2-fluoro-5-(2-fluoro-4-heptylphenyl)-pyridine
2-trifluoromethyl-5-(4-ethoxyphenyl)-pyridine
2-trifluoromethyl-5-(4-propoxyphenyl)-pyridine
2-trifluoromethyl-5-(4-butoxyphenyl)-pyridine
2-trifluoromethyl-5-(4-ethylphenyl)-pyridine
2-trifluoromethyl-5-(4-propylphenyl)-pyridine
2-trifluoromethyl-5-(4-butylphenyl)-pyridine
2-trifluoromethyl-5-(4-pentylphenyl)-pyridine
2-trifluoromethyl-5-(4-hexylphenyl)-pyridine
2-trifluoromethyl-5-(4-heptylphenyl)-pyridine
2-trifluoromethoxy-5-(4-ethylphenyl)-pyridine
2-trifluoromethoxy-5-(4-propylphenyl)-pyridine
2-trifluoromethoxy-5-(4-butylphenyl)-pyridine
2-trifluoromethoxy-5-(4-pentylphenyl)-pyridine
2-difluoromethoxy-5-(4-ethylphenyl)-pyridine
2-difluoromethoxy-5-(4-propylphenyl)-pyridine
2-difluoromethoxy-5-(4-butylphenyl)-pyridine
2-difluoromethoxy-5-(4-pentylphenyl)-pyridine
2-difluoromethoxy-5-(4-hexylphenyl)-pyridine
2-difluoromethoxy-5-(4-ethoxyphenyl)-pyridine

EXAMPLE 2

To a mixture of 0.1 M of 2,6-difluoro-3-hydroxypyridine (obtainable by reaction of 2,6-difluoro-pyridine-3-boronic acid with $H_2O_2$ in ether), 0.1 M of trans-4-pentylcyclohexane carboxylic acid, 0.1 M dimethylaminopyridine (DMAP) and 200 ml of C a solution of 0.11 M of dicyclohexylcarbodiimide (DCC) in C is added at 15°–20° C.

After stirring for 5 hours at room temperature and customary work-up, 2,6-difluoropyridine-3-yl trans-4-pentylcyclohexanecarboxylate is obtained.

The following components are obtained analogously:
2,6-difluoropyridine-3-yl trans-4-ethylcyclohexanecarboxylate
2,6-difluoropyridine-3-yl trans-4-propylcyclohexanecarboxylate
2,6-difluoropyridine-3-yl trans-4-butylcyclohexanecarboxylate
2,6-difluoropyridine-3-yl trans-4-(trans-4-ethylcyclohexyl)-cyclohexanecarboxylate
2,6-difluoropyridine-3-yl trans-4-(trans-4-propylcyclohexyl)-cyclohexanecarboxylate
2,6-difluoropyridine-3-yl trans-4-(trans-4-butylcyclohexyl)-cyclohexanecarboxylate
2,6-difluoropyridine-3-yl trans-4-(trans-4-pentylcyclohexyl)-cyclohexanecarboxylate
2-fluoropyridine-5-yl trans-4-(trans-4-ethylcyclohexyl)-cyclohexanecarboxylate
2-fluoropyridine-5-yl trans-4-(trans-4-propylcyclohexyl)cyclohexanecarboxylate
2-fluoropyridine-5-yl trans-4-(trans-4-butylcyclohexyl)-cyclohexanecarboxylate
2-fluoropyridine-5-yl trans-4-(trans-4-pentylcyclohexyl)cyclohexanecarboxylate
2-fluoropyridine-5-yl trans-4-(trans-4-heptylcyclohexyl)cyclohexanecarboxylate
2-chloropyridine-5-yl trans-4-(trans-4-ethylcyclohexyl)-cyclohexanecarboxylate
2-chloropyridine-5-yl trans-4-(trans-4-propylcyclohexyl)cyclohexanecarboxylate
2-chloropyridine-5-yl trans-4-(trans-4-butylcyclohexyl)cyclohexanecarboxylate
2-chloropyridine-5-yl trans-4-(trans-4-pentylcyclohexyl)cyclohexanecarboxylate
2-chloropyridine-5-yl trans-4-(trans-4-octylcyclohexyl)cyclohexanecarboxylate
2-trifluoromethylpyridine-5-yl trans-4-ethylcyclohexanecarboxylate
2-trifluoromethylpyridine-5-yl trans-4-propylcyclohexanecarboxylate
2-trifluoromethylpyridine-5-yl trans-4-butylcyclohexanecarboxylatecarboxylate
2-trifluoromethylpyridine-5-yl trans-4-pentylcyclohexanecarboxylate
2-trifluoromethylpyridine-5-yl trans-4-hexylcyclohexanecarboxylate
2-trifluoromethoxypyridine-5-yl trans-4-propylcyclohexanecarboxylate
2-trifluoromethoxypyridine-5-yl trans-4-butylcyclohexanecarboxylate
2-trifluoromethoxypyridine-5-yl trans-4-pentylcyclohexanecarboxylate
2-trifluoromethoxypyridine-5-yl trans-4-hexylcyclohexanecarboxylate
2-difluoromethoxypyridine-5-yl trans-4-propylcyclohexanecarboxylate 2-difluoromethoxypyridine-5-yl trans-4-butylcyclohexanecarboxylate
2-difluoromethoxypyridine-5-yl trans-4-pentylcyclohexanecarboxylate
2-difluoromethoxypyridine-5-yl trans-4-hexylcyclohexanecarboxylate
2-difluoromethoxypyridine-5-yl trans-4-heptylcyclohexanecarboxylate
2-fluoro-6-chloropyridine-3-yl trans-4-ethylcyclohexanecarboxylate
2-fluoro-6-chloropyridine-3-yl trans-4-propylcyclohexanecarboxylate
2-fluoro-6-chloropyridine-3-yl trans-4-butylcyclohexanecarboxylate
2-fluoro-6-chloropyridine-3-yl trans-4-pentylcyclohexanecarboxylate
2,6-difluoropyridine-3-yl 4-ethylbenzoate
2,6-difluoropyridine-3-yl 4-propylbenzoate
2,6-difluoropyridine-3-yl 4-butylbenzoate
2,6-difluoropyridine-3-yl 4-pentylbenzoate
2,6-difluoropyridine-3-yl 4-ethoxybenzoate
2,6-difluoropyridine-3-yl 4-propoxybenzoate
2,6-difluoropyridine-3-yl 4-butoxybenzoate
2,6-difluoropyridine-3-yl 4-pentyloxybenzoate
2,6-difluoropyridine-3-yl 4-hexyloxybenzoate
2,6-difluoropyridine-3-yl 4-heptyloxybenzoate
2,6-difluoropyridine-3-yl 4-octyloxybenzoate
2-fluoropyridine-5-yl 4-ethylbenzoate
2-fluoropyridine-5-yl 4-propylbenzoate
2-fluoropyridine-5-yl 4-butylbenzoate
2-fluoropyridine-5-yl 4-pentylbenzoate
2-fluoropyridine-5-yl 4-ethoxybenzoate
2-fluoropyridine-5-yl 4-propoxybenzoate
2-fluoropyridine-5-yl 4-butoxybenzoate
2-fluoropyridine-5-yl 4-pentyloxybenzoate
2-fluoropyridine-5-yl 4-hexyloxybenzoate
2-fluoropyridine-5-yl 4-heptyloxybenzoate
2-fluoropyridine-5-yl 4-octyloxybenzoate
2-trifluoromethylpyridine-5-yl 4-ethylbenzoate
2-trifluoromethylpyridine-5-yl 4-propylbenzoate
2-trifluoromethylpyridine-5-yl 4-butylbenzoate
2-trifluoromethylpyridine-5-yl 4-pentylbenzoate
2-trifluoromethoxypyridine-5-yl 4-ethoxybenzoate
2-trifluoromethoxypyridine-5-yl 4-propoxybenzoate
2-trifluoromethoxypyridine-5-yl 4-butoxybenzoate
2-trifluoromethoxypyridine-5-yl 4-penthyloxybenzoate
2-trifluoromethoxypyridine-5-yl- 4-hexyloxybenzoate
2-trifluoromethoxypyridine-5-yl 4-heptyloxybenzoate
2-trifluoromethoxypyridine-5-yl 4-octyloxybenzoate
2-difluoromethoxypyridine-5-yl 4-ethoxybenzoate
2-difluoromethoxypyridine-5-yl 4-propoxybenzoate
2-difluoromethoxypyridine-5-yl 4-butoxybenzoate
2-difluoromethoxypyridine-5-yl 4-pentoxybenzoate
2-difluoromethoxypyridine-5-yl 4-hexoxybenzoate
2-difluoromethoxypyridine-5-yl 4-heptoxybenzoate
2-fluoropyridine-5-yl trans-4-ethylcyclohexanecarboxylate
2-fluoropyridine-5-yl trans-4-propylcyclohexanecarboxylate
2-fluoropyridine-5-yl trans-4-butylcyclohexanecarboxylate
2-fluoropyridine-5-yl trans-4-pentylcyclohexanecarboxylate
2-trifluoromethylpyridine-5-yl trans-4-(trans-4-ethylcyclohexyl)-cyclohexanecarboxylate
2-trifluoromethylpyridine-5-yl trans-4-(trans-4-propylcyclohexyl)-cyclohexanecarboxylate
2-trifluoromethylpyridine-5-yl trans-4-(trans-4-butylcyclohexyl)-cyclohexanecarboxylate
2-trifluoromethylpyridine-5-yl trans-4-(trans-4-pentylcyclohexyl)-cyclohexanecarboxylate
2-chloropyridine-5-yl 4-(4-ethylphenyl)benzoate
2-chloropyridine-5-yl 4-(4-propylphenyl)benzoate
2-chloropyridine-5-yl 4-(4-butylphenyl)benzoate
2-chloropyridine-5-yl 4-(4-pentylphenyl)benzoate
2-chloropyridine-5-yl 4-(4-octylphenyl)benzoate
6-chloro-2-fluoropyridine-3-yl 4-(4-ethylphenyl)benzoate
6-chloro-2-fluoropyridine-3-yl 4-(4-propylphenyl)benzoate
6-chloro-2-fluoropyridine-3-yl 4-(4-butylphenyl)benzoate
6-chloro-2-fluoropyridine-3-yl 4-(4-pentylphenyl)benzoate
6-chloro-2-fluoropyridine-3-yl 4-(4-heptylphenyl)benzoate
2,6-difluoropyridine-3-yl 4-(trans-4-ethylcyclohexyl)-benzoate
2,6-difluoropyridine-3-yl 4-(trans-4-propylcyclohexyl)-benzoate
2,6-difluoropyridine-3-yl 4-(trans-4-butylcyclohexyl)-benzoate
2,6-difluoropyridine-3-yl 4-(trans-4-pentylcyclohexyl)-benzoate
2,6-difluoropyridine-3-yl trans-4-(4-ethylphenyl)cyclohexanecarboxylate
2,6-difluoropyridine-3-yl trans-4-(4-propylphenyl)cyclohexanecarboxylate
2,6-difluoropyridine-3-yl trans-4-(4-butylphenyl)cyclohexanecarboxylate
2,6-difluoropyridine-3-yl trans-4-(4-pentylphenyl)cyclohexanecarboxylate Example 3 a) 0,6 M of n-butyllithium are added at −10° to 0,6 M of diisopropylamin in 600 ml THF. The mixture is cooled to −70°, 0,6 M of 2,6-difluoropyridin are added and after stirring for 15 minutes 0,6 M of trimethylborate are added at the same temperature. The mixture is allowed to warm up to −30°. Then the borate ester is hydrolysed with dilute HCl, the product extracted with ether, washed, dried and the solvent removed. Thus, 2,6-difluoro-pyridine-3-boronic acid is obtained.

b) A mixture of 0,05 M of 4-(trans-4-pentylcyclohexyl)bromobenzene, 0,06 M of 2,6-difluoropyridine-3-boronic acid, 1,25 g of Pd(PPh₃)₄, 100 ml of toluene, 40 ml of ethanol and 50 ml of 2 M Na₂CO₃-solution is heated at 60 °C under stirring for 2 hours. Customary work-up and recrystallisation from ethanol gives 2,6-difluoro-3-[4-(trans-4-pentylcyclohexyl)phenyl]-pyridine with C 58° N 107° I.

The following compounds are obtained analogously:
2,6-difluoro-3-[4-(trans-4-ethylcyclohexyl)phenyl]-pyridine
2,6-difluoro-3-[4-(trans-4-propylcyclohexyl)phenyl]-pyridine
2,6-difluoro-3-[4-(trans-4-butylcyclohexyl)phenyl]-pyridine
6-chloro-2-fluoro-3-[4-(trans-4-ethylcyclohexyl)-phenyl]-pyridine
6-chloro-2-fluoro-3-[4-(trans-4-propylcyclohexyl)-phenyl]-pyridine
6-chloro-2-fluoro-3-[4-(trans-4-butylcyclohexyl)phenyl-pyridine 6-chloro-2-fluoro-3-[4-(trans-4-pentylcyclohexyl)-phenyl]-pyridine
6-chloro-2-fluoro-3-[4-(trans-4-hexylcyclohexyl)-phenyl]-pyridine
2,6-difluroro-3-[4-(trans-4-ethylcyclohexylethyl)-phenyl]-pyridine
2,6-difluroro-3-[4-(trans-4-propylcyclohexylethyl)phenyl-pyridine
2,6-difluroro-3-[4-(trans-4-butylcyclohexylethyl)phenyl-pyridine
2,6-difluroro-3-4-(trans-4-pentylcyclohexylethyl)-phenyl]-pyridine
2,6-difluroro-3-[4-(trans-4-octylcyclohexylethyl)-phenyl]-pyridine
6-chloro-2-fluoro-3-[4-(trans-4-ethylcyclohexylethyl)-phenyl]-pyridine
6-chloro-2-fluoro-3-[4-(trans-4-propylcyclohexylethyl)-phenyl]-pyridine
6-chloro-2-fluoro-3-[4-(trans-4-butylcyclohexylethyl)-phenyl]-pyridine
6-chloro-2-fluoro-3-[4-(trans-4-pentylcyclohexylethyl)-phenyl]-pyridine
2,6-difluoro-3-[4-(trans-4-ethylcyclohexyl)-2-fluoro-phenyl]-pyridine
2,6-difluoro-3-[4-(trans-4-propylcyclohexyl)-2-fluoro-phenyl]-pyridine
2,6-difluoro-3-4-(trans-4-butylcyclohexyl)-2-fluoro-phenyl]-pyridine
2,6-difluoro-3-4-(trans-4-pentylcyclohexyl)-2-fluoro-phenyl]-pyridine
2,6-difluoro-3-[4-(trans-4-heptylcyclohexyl)-2-fluoro-phenyl]-pyridine
2,6-difluoro-3-(4-ethylbiphenyl-4'-yl)-pyridine
2,6-difluoro-3-(4-propylbiphenyl-4'-yl)-pyridine
2,6-difluoro-3-(4-butylbiphenyl-4'-yl)-pyridine
2,6-difluoro-3-(4-pentylbiphenyl-4'-yl)-pyridine
2,6-difluoro-3-(4-ethoxybiphenyl-4'-yl)-pyridine
2,6-difluoro-3-(4-propoxybiphenyl-4'-yl)-pyridine
2,6-difluoro-3-(4-butoxybiphenyl-4'-yl)-pyridine
2,6-difluoro-3-(4-pentyloxybiphenyl-4'-yl)-pyridine
2,6-difluoro-3-(4-hexyloxybiphenyl-4'-yl)-pyridine
2,6-difluoro-3-(4-heptyloxybiphenyl-4'-yl)-pyridine
2,6-difluoro-3-(4-octyloxybiphenyl-4'-yl)-pyridine
2,6-difluoro-3-(4-ethylphenyl)-pyridine
2,6-difluoro-3-(4-propylphenyl)-pyridine
2,6-difluoro-3-(4-butylphenyl)-pyridine
2,6-difluoro-3-(4-pentylphenyl)-pyridine
6-chloro-2-fluoro-3-(4-ethylphenyl)-pyridine
6-chloro-2-fluoro-3-(4-propylphenyl)-pyridine
6-chloro-2-fluoro-3-(4-butylphenyl)-pyridine
6-chloro-2-fluoro-3-(4-pentylphenyl)-pyridine
6-chloro-2-fluoro-3-(4-hexylphenyl)-pyridine
2,6-difluoro-3-(4-ethoxyphenyl)-pyridine
2,6-difluoro-3-(4-propoxyphenyl)-pyridine
2,6-difluoro-3-(4-butoxyphenyl)-pyridine
2,6-difluoro-3-(4-pentyloxyphenyl)-pyridine
2,6-difluoro-3-(4-octyloxyphenyl)-pyridine Example 4

0,2 mM of Pd(Ph3P)2Cl2 and 0,1 mM of CuJ are added to a mixture of 0,01 M of 3-bromo-2,6-difluoropyridine (preparation: 2,6-difluoropyridine is reacted with lithiumdiisopropylamide (LDA) as described in example 3a, then Br2 is added at −60° to −70°. The mixture is allowed to warm up to room temperature and worked up, the product is purified by distillation), 0,01 M of 4-pentylphenylacetylene and 200 ml of triethylamine. The mixture is stirred for 8 hours at room temperature; after customary work-up and purification by crystallization and chromatography 1-(4-pentylphenyl)-2-(2,6-difluoropyridine-3-yl)acetylene is obtained.

The following compounds are obtained analogously:
1-(4-ethylphenyl)-2-(2,6-difluoropyridine-3-yl)acetylene
1-(4-propylphenyl)-2-(2,6-difluoropyridine-3-yl)acetylene
1-(4-butylphenyl)-2-(2,6-difluoropyridine-3-yl)acetylene
1-(4-hexylphenyl)-2-(2,6-difluoropyridine-3-yl)acetylene
1-(4-ethoxyphenyl)-2-(2,6-difluoropyridine-3-yl)acetylene
1-(4-butoxyphenyl)-2-(2,6-difluoropyridine-3-yl)acetylene
1-(4-methoxyphenyl)-2-(2,6-difluoropyridine-3-yl)acetylene
1-(4-propoxyphenyl)-2-(2,6-difluoropyridine-3-yl)acetylene
1-(4-pentyloxyphenyl)-2-(2,6-difluoropyridine-3-yl)-acetylene
1-(4-ethylphenyl)-2-(6-chloro-2-fluoropyridine-3-yl)acetylene
1-(4-propylphenyl)-2-(6-chloro-2-fluoropyridine-3-yl)acetylene
1-(4-butylphenyl)-2-(6-chloro-2-fluoropyridine-3-yl)acetylene
1-(4-pentylphenyl)-2-(6-chloro-2-fluoropyridine-3-yl)acetylene
1-(4-ethylbiphenyl-4'-yl)-2-(2,6-difluoropyridine-3-yl)acetylene
1-(4-propylbiphenyl-4'-yl)-2-(2,6-difluoropyridine-3-yl)acetylene
1-(4-butylbiphenyl-4'-yl)-2-(2,6-difluoropyridine-3-yl)acetylene
1-(4-pentylbiphenyl-4'-yl)-2-(2,6-difluoropyridine-3-yl)acetylene
1-(4-ethoxybiphenyl-4'-yl)-2-(2,6-difluoropyridine-3-yl)acetylene
1-(4-propoxybiphenyl-4'-yl)-2-(2,6-difluoropyridine-3-yl)acetylene
1-(4-butoxybiphenyl-4'-yl)-2-(2,6-difluoropyridine-3-yl)acetylene
1-(4-pentyloxybiphenyl-4'-yl)-2-(2,6-difluoropyridine-3-yl)acetylene
1-[4-(trans-4-ethylcyclohexyl)phenyl]-2-(2,6-difluoropyridine-3-yl)acetylene
1-[4-(trans-4-propylcyclohexyl)phenyl]-2-(2,6-difluoropyridine-3-yl)acetylene
1-[4-(trans-4-butylcyclohexyl)phenyl]-2-(2,6-difluoropyridine-3-yl)acetylene
1-[4-(trans-4-pentylcyclohexyl)phenyl]-2-(2,6-difluoropyridine-3-yl)acetylene
1-[trans-4-(4-ethylphenyl)cyclohexyl]-2-(2,6-difluoropyridine-3-yl)acetylene
1-[trans-4-(4-propylphenyl)cyclohexyl]-2-(2,6-difluoropyridine-3-yl)acetylene
1-[trans-4-(4-butylphenyl)cyclohexyl]-2-(2,6-difluoropyridine-3-yl)acetylene
1-[trans-4-(4-pentylphenyl)cyclohexyl]-2-(2,6-difluoropyridine-3-yl)acetylene
1-[trans-4-(4-hexylphenyl)cyclohexyl]-2-(2,6-difluoropyridine-3-yl)acetylene
1-[trans-4-(trans-4-ethylcyclohexyl)cyclohexyl]-2-(2,6-difluoropyridine-3-yl)acetylene 1-[trans-4-(trans-4-propylcyclohexyl)cyclohexyl]-2-(2,6-difluoropyridine-3-yl)acetylene
1-[trans-4-(trans-4-butylcyclohexyl)cyclohexyl]-2-(2,6-difluoropyridine-3-yl)acetylene
1-trans-4-(trans-4-pentylcyclohexyl)cyclohexyl]-2-(2,6-difluoropyridine-3-yl)acetylene
1-[trans-4-(trans-4-heptylcyclohexyl)cyclohexyl]-2-(2,6-difluoropyridine-3-yl)acetylene
1-(trans-4-ethylcyclohexyl)-2-(2,6-difluoropyridine3-yl)acetylene
1-(trans-4-propylcyclohexyl)-2-(2,6-difluoropyridine3-yl)acetylene
1-(trans-4-butylcyclohexyl)-2-(2,6-difluoropyridine3-yl)acetylene
1-(trans-4-pentylcyclohexyl)-2-(2,6-difluoropyridine3-yl)acetylene
1-trans-4-(4-ethoxyphenyl)cyclohexyl]-2-(2,6-difluoropyridine-3-yl)acetylene
1-[trans-4-(4-propoxyphenyl)cyclohexyl]-2-(2,6-difluoropyridine-3-yl)acetylene
1-[trans-4-(4-butoxyphenyl)cyclohexyl]-2-(2,6-difluoropyridine-3-yl)acetylene
1-[trans-4-(4-pentyloxyphenyl)cyclohexyl]-2-(2,6-difluoropyridine-3-yl)acetylene
1-[trans-4-(4-octyloxyphenyl)cyclohexyl]-2-(2,6-difluoropyridine-3-yl)acetylene
1-[4-(trans-4-ethylcyclohexyl)phenyl)-2-(6-chloro-2-fluoropyridine-3-yl)acetylene
1-[4-(trans-4-propylcyclohexyl)phenyl)-2-(6-chloro-2-fluoropyridine-3-yl)acetylene
1-[4-(trans-4-butylcyclohexyl)phenyl)-2-(6-chloro-2-fluoropyridine-3-yl)acetylene
1-[4-(trans-4-pentylcyclohexyl)phenyl)-2-(6-chloro-2-fluoropyridine-3-yl)acetylene Example 5

Hydrogenation of 1-(4-pentylphenyl)-2-(2,6-difluoropyridine-3-yl)acetylene yields after customary work-up 1-(4-pentylphenyl)-2-(2,6-difluoropyridine-3-yl)ethane.

The following compounds are obtained analogously:
1-(4-ethylphenyl)-2-(2,6-difluoropyridine-3-yl)ethane
1-(4-propylphenyl)-2-(2,6-difluoropyridine-3-yl)ethane
1-(4-butylphenyl)-2-(2,6-difluoropyridine-3-yl)ethane
1-(4-hexylphenyl)-2-(2,6-difluoropyridine-3-yl)ethane
1-(4-ethoxyphenyl)-2-(2,6-difluoropyridine-3-yl)ethane
1-(4-butoxyphenyl)-2-(2,6-difluoropyridine-3-yl)ethane
1-(4-methoxyphenyl)-2-(2,6-difluoropyridine-3-yl)ethane
1-(4-propoxyphenyl)-2-(2,6-difluoropyridine-3-yl)ethane
1-(4-pentyloxyphenyl)-2-(2,6-difluoropyridine-3-yl)ethane
1-(4-ethylphenyl)-2-(6-chloro-2-fluoropyridine-3-yl)ethane
1-(4-propylphenyl)-2-(6-chloro-2-fluoropyridine-3-yl)ethane
1-(4-butylphenyl)-2-(6-chloro-2-fluoropyridine-3-yl)ethane
1-(4-pentylphenyl)-2-(6-chloro-2-fluoropyridine-3-yl)ethane
1-(4-ethylbiphenyl-4'-yl)-2-(2,6-difluoropyridine-3-yl)ethane
1-(4-propylbiphenyl-4'-yl)-2-(2,6-difluoropyridine-3-yl)ethane
1-(4-butylbiphenyl-4'-yl)-2-(2,6-difluoropyridine-3-yl)ethane
1-(4-pentylbiphenyl-4'-yl)-2-(2,6-difluoropyridine-3-yl)ethane
1-(4-ethoxybiphenyl-4'-yl)-2-(2,6-difluoropyridine-3-yl)ethane
1-(4-propoxybiphenyl-4'-yl)-2-(2,6-difluoropyridine-3-yl)ethane
1-(4-butoxybiphenyl-4'-yl)-2-(2,6-difluoropyridine-3-yl)ethane
1-(4-pentyloxybiphenyl-4'-yl)-2-(2,6-difluoropyridine-3-yl)ethane
1-[4-(trans-4-ethylcyclohexyl)phenyl]-2-(2,6-difluoropyridine-3-yl)ethane
1-[4-(trans-4-propylcyclohexyl)phenyl]-2-(2,6-difluoropyridine-3-yl)ethane
1-[4-(trans-4-butylcyclohexyl)phenyl]-2-(2,6-difluoropyridine-3-yl)ethane
1-[4-(trans-4-pentylcyclohexyl)phenyl]-2-(2,6-difluoropyridine-3-yl)ethane
1-trans-4-(4-ethylphenyl)cyclohexyl]-2-(2,6-difluoropyridine-3-yl)ethane
1-[trans-4-(4-propylphenyl)cyclohexyl]-2-(2,6-difluoropyridine-3-yl)ethane
1-[trans-4-(4-butylphenyl)cyclohexyl]-2-(2,6-difluoropyridine-3-yl)ethane
1-[trans-4-(4-pentylphenyl)cyclohexyl]-2-(2,6-difluoropyridine-3-yl)ethane
1-trans-4-(4-hexylphenyl)cyclohexyl]-2-(2,6-difluoropyridine-3-yl)ethane
1-[trans-4-(trans-4-ethylcyclohexyl)cyclohexyl]-2-(2,6-difluoropyridine-3-yl)ethane
1-[trans-4-(trans-4-propylcyclohexyl)cyclohexyl]-2-(2,6-difluoropyridine-3-yl)ethane
1-[trans-4-(trans-4-butylcyclohexyl)cyclohexyl]-2-(2,6-difluoropyridine-3-yl)ethane
1-[trans-4-(trans-4-pentylcyclohexyl)cyclohexyl]-2-(2,6-difluoropyridine-3-yl)ethane
1-[trans-4-(trans-4-heptylcyclohexyl)cyclohexyl]-2-(2,6-difluoropyridine-3-yl)ethane
1-(trans-4-ethylcyclohexyl)-2-(2,6-difluoropyridine-3-yl)ethane
1-(trans-4-propylcyclohexyl)-2-(2,6-difluoropyridine-3-yl)ethane
1-(trans-4-butylcyclohexyl)-2-(2,6-difluoropyridine-3-yl)ethane
1-(trans-4-pentylcyclohexyl)-2-(2,6-difluoropyridine-3-yl)ethane
1-[trans-4-(4-ethoxyphenyl)cyclohexyl]-2-(2,6-difluoropyridine-3-yl)ethane
1-[trans-4-(4-propoxyphenyl)cyclohexyl]-2-(2,6-difluoropyridine-3-yl)ethane
1-[trans-4-(4-butoxyphenyl)cyclohexyl]-2-(2,6-difluoropyridine-3-yl)ethane
1-[trans-4-(4-pentyloxyphenyl)cyclohexyl]-2-(2,6-difluoropyridine-3-yl)ethane
1-[trans-4-(4-octyloxyphenyl)cyclohexyl]-2-(2,6-difluoropyridine-3-yl)ethane
1-[4-(trans-4-ethylcyclohexyl)phenyl]-2-(6-chloro-2-fluoropyridine-3-yl)ethane
1-4-(trans-4-propylcyclohexyl)phenyl)-2-(6-chloro-2-fluoropyridine-3-yl)-ethane
1-4-(trans-4-butylcyclohexyl)phenyl)-2-(6-chloro-2-fluoropyridine-3-yl )ethane
1-[4-(trans-4-pentylcyclohexyl)phenyl)-2-(6-chloro-2-fluoropyridine-3-yl)ethane Example 6

Analogously to Example 4 1-(4-pentylphenyl)-2-(2-fluoropyridine-5-yl)acetylene is obtained by reacting 2-fluoro5-bromopyridine (preparation described in example 1a) with 4-pentylphenylacetylene.

The following compounds are obtained analogously:
1-(4-ethylphenyl)-2-(2-fluoropyridine-5-yl)acetylene
1-(4-propylphenyl)-2-(2-fluoropyridine-5-yl)acetylene
1-(4-butylphenyl)-2-(2-fluoropyridine-5-yl)acetylene
1-(4-heptylphenyl)-2-(2-fluoropyridine-5-yl)acetylene
1-(4-ethoxyphenyl)-2-(2-fluoropyridine-5-yl)acetylene
1-(4-propoxyphenyl)-2-(2-fluoropyridine-5-yl)acetylene
1-(4-butoxyphenyl)-2-(2-fluoropyridine-5-yl)acetylene
1-(4-pentyloxyphenyl)-2-(2-fluoropyridine-5-yl)acetylene
1-(4-ethylphenyl)-2-(2-chloropyridin-5-yl)acetylene
1-(4-propylphenyl)-2-(2-chloropyridin-5-yl)acetylene
1-(4-butylphenyl)-2-(2-chloropyridin-5-yl)acetylene
1-(4-pentylphenyl)-2-(2-chloropyridin-5-yl)acetylene
1-(4-ethoxyphenyl)-2-(2-trifluoromethylpyridine-5-yl)acetylene
1-(4-propoxyphenyl)-2-(2-trifluoromethylpyridine-5-yl)acetylene
1-(4-butoxyphenyl)-2-(2-trifluoromethylpyridine-5-yl)acetylene
1-(4-pentyloxyphenyl)-2-(2-trifluoromethylpyridine-5-yl)acetylene
1(4-ethoxyphenyl)-2-(2-trifluormethoxypyridine-5-yl)acetylene
1-(4-propoxyphenyl)-2-(2-trifluormethoxypyridine-5-yl)acetylene
1-(4-butoxyphenyl)-2-(2-trifluormethoxypyridine-5-yl)acetylene
1-(4-pentyloxyphenyl)-2-(2-trifluormethoxypyridine-5-yl)acetylene
1-(4-propyloxyphenyl)-2-(2-trifluormethoxpyridine-5-yl)acetylene
1-(4-ethoxyphenyl)-2-(2-chloropyridine-5-yl)acetylene
1-(4-propoxyphenyl)-2-(2-chloropyridine-5-yl)acetylene
1-(4-butoxyphenyl)-2-(2-chloropyridine-5-yl)acetylene
1-(4-pentyloxyphenyl)-2-(2-chloropyridine-5-yl)acetylene
1-(4-ethylbiphenyl-4'-yl)-2-(2-fluoropyridine-5-yl)acetylene
1-(4-propylbiphenyl-4'-yl)-2-(2-fluoropyridine-5-yl)acetylene
1-(4-butylbiphenyl-4'-yl)-2-(2-fluoropyridine-5-yl)acetylene
1-(4-pentylbiphenyl-4'-yl)-2-(2-fluoropyridine-5-yl)acetylene
1-(4-ethylbiphenyl-4'-yl)-2-(2-trifluoromethylpyridine-5-yl)acetylene
1-(4-propylbiphenyl-4'-yl)-2-(2-trifluoromethylpyridine-5-yl)acetylene
1-(4-butylbiphenyl-4'-yl)-2-(2-trifluoromethylpyridine-5-yl)acetylene
1-(4-pentylbiphenyl-4'-yl)-2-(2-trifluoromethylpyridine-5-yl)acetylene
1-(4-ethylbiphenyl-4'-yl)-2-(2-trifluoromethoxypyridine-5-yl)acetylene
1-(4-propylbiphenyl-4'-yl)-2-(2-trifluoromethoxypyridine-5-yl)acetylene
1-(4-butylbiphenyl-4'-yl)-2-(2-trifluoromethoxypyridine-5-yl)acetylene
1(4-pentylbiphenyl-4'-yl)-2-(2-trifluoromethoxypyridine-5-yl)acetylene
1-(4-hexylbiphenyl-4'-yl)-2-(2-trifluoromethoxypyridine-5-yl)acetylene
1-[4-(trans-4-ethylcyclohexyl)phenyl]-2-[2-fluoropyridine-5-yl]acetylene
1-[4-(trans-4-propylcyclohexyl)phenyl]-2-[2-fluoropyridine-5-yl]acetylene
1-[4-(trans-4-butylcyclohexyl)phenyl]-2-[2-fluoropyridine-5-yl]acetylene
1-[4-(trans-4-pentylcyclohexyl)phenyl]-2-[2-fluoropyridine-5-yl]acetylene
1-4-(trans-4-octylcyclohexyl)phenyl]-2-[2-fluoropyridine-5-yl]acetylene
1-trans-4-(4-ethylphenyl)cyclohexyl]-2-(2-chloropyridine-5-yl)acetylene
1-[trans-4-(4-propylphenyl)cyclohexyl]-2-(2-chloropyridine-5-yl)acetylene
1-[trans-4-(4-butylphenyl)cyclohexyl]-2-(2-chloropyridine-5-yl)acetylene
1-[trans-4-(4-pentylphenyl)cyclohexyl]-2-(2-chloropyridine-5-yl)acetylene
1-[trans-4-(4-ethoxyphenyl)cyclohexyl]-2-(2-fluoropyridine-5-yl)acetylene
1-[trans-4-(4-propoxyphenyl)cyclohexyl]-2-(2-fluoropyridine-5-yl)acetylene
1-[trans-4-(4-butoxyphenyl)cyclohexyl]-2-(2-fluoropyridine-5-yl)acetylene
1-[trans-4-(4-pentyloxyphenyl)cyclohexyl]-2-(2-fluoropyridine-5-yl)acetylene
1-(trans-4-ethylcyclohexyl)-2-(2-fluoropyridine-5-yl)acetylene
1-(trans-4-propylcyclohexyl)-2-(2-fluoropyridine-5-yl)acetylene
1-(trans-4-butylcyclohexyl)-2-(2-fluoropyridine-5-yl)acetylene
1-(trans-4-pentylcyclohexyl)-2-(2-fluoropyridine-5-yl)acetylene
1-[trans-4-(trans-4-ethylcyclohexyl)cyclohexyl]-2-(2-trifluoromethylpyridine-5-yl)acetylene
1-[trans-4-(trans-4-propylcyclohexyl)cyclohexyl]-2-(2-trifluoromethylpyridine-5-yl)acetylene
1-[trans-4-(trans-4-butylcyclohexyl)cyclohexyl-2-(2-trifluoromethylpyridine-5-yl)acetylene
1-[trans-4-(trans-4-pentylcyclohexyl)cyclohexyl]-2-(2-trifluoromethylpyridine-5-yl)acetylene
1-[trans-4-(trans-4-heptylcyclohexyl)cyclohexyl]-2-(2-trifluoromethylpyridine-5-yl)acetylene
1-[trans-4-(trans-4-ethylcyclohexyl)cyclohexyl]-2-(2-fluoropyridine-5-yl)acetylene
1-[trans-4-(trans-4-propylcyclohexyl)cyclohexyl]-2-(2-fluoropyridine-5-yl)acetylene
1-[trans-4-(trans-4-butylcyclohexyl)cyclohexyl]-2-(2-fluoropyridine-5-yl)acetylene
1-[trans-4-(trans-4-pentylcyclohexyl)cyclohexyl]-2-(2-fluoropyridine-5-yl)acetylene Example 7

Hydrogenation of 1-(4-pentylphenyl)-2-(2-fluoropyridine5-yl)acetylene yields after customary work-up 1-(4-pentylphenyl)-2-(2-fluoropyridine-5-yl)ethane The following compounds are prepared analogously:
1-(4-ethylphenyl)-2-(2-fluoropyridine-5-yl)ethane
1-(4-propylphenyl)-2-(2-fluoropyridine-5-yl)ethane
1-(4-butylphenyl)-2-(2-fluoropyridine-5-yl)ethane
1-(4-heptylphenyl)-2-(2-fluoropyridine-5-yl)ethane
1-(4-ethoxyphenyl)-2-(2-fluoropyridine-5-yl)ethane
1-(4-propoxyphenyl)-2-(2-fluoropyridine-5-yl)ethane
1-(4-butoxyphenyl)-2-(2-fluoropyridine-5-yl)ethane
1-(4-pentyloxyphenyl)-2-(2-fluoropyridine-5-yl)ethane
1-(4-ethylphenyl)-2-(2-chloropyridin-5-yl)ethane
1-(4-propylphenyl)-2-(2-chloropyridin-5-yl)ethane
1-(4-butylphenyl)-2-(2-chloropyridin-5-yl)ethane 1-(4-pentylphenyl)-2-(2-chloropyridin-5-yl)ethane
1-(4-ethoxyphenyl)-2-(2-trifluoromethylpyridine-5-yl)ethane
1-(4-propoxyphenyl)-2-(2-trifluoromethylpyridine-5-yl)ethane
1-(4-butoxyphenyl)-2-(2-trifluoromethylpyridine-5-yl)ethane
1-(4-pentyloxyphenyl)-2-(2-trifluoromethylpyridine-5-yl)ethane
1-(4-ethoxyphenyl)-2-(2-chloropyridine-5-yl)ethane
1-(4-propoxyphenyl)-2-(2-chloropyridine-5-yl)ethane
1-(4-butoxyphenyl)-2-(2-chloropyridine-5-yl)ethane
1-(4-pentyloxyphenyl)-2-(2-chloropyridine-5-yl)ethane
1-(4-ethylbiphenyl-4'-yl)-2-(2-fluoropyridine-5-yl)ethane
1-(4-propylbiphenyl-4'-yl)-2-(2-fluoropyridine-5-yl)ethane
1-(4-butylbiphenyl-4'-yl)-2-(2-fluoropyridine-5-yl)ethane
1-(4-pentylbiphenyl-4'-yl)-2-(2-fluoropyridine-5-yl)ethane
1-(4-ethylbiphenyl-4'-yl)-2-(2-trifluoromethylpyridine-5yl)ethane
1-(4-propylbiphenyl-4'-yl)-2-(2-trifluoromethylpyridine-5-yl)ethane
1-(4-butylbiphenyl-4'-yl)-2-(2-trifluoromethylpyridine-5-yl)ethane
1-(4-pentylbiphenyl-4'-yl)-2-(2-trifluoromethylpyridine-5-yl)ethane
1-(4-ethylbiphenyl-4'-yl)-2-(2-trifluoromethoxypyridine-5-yl)ethane
1-(4-propylbiphenyl-4'-yl)-2-(2-trifluoromethoxypyridine-5-yl)ethane
1-(4-butylbiphenyl-4'-yl)-2-(2-trifluoromethoxypyridine-5-yl)ethane
1-(4-pentylbiphenyl-4'-yl)-2-(2-trifluoromethoxypyridine-5-yl)ethane
1-(4-hexylbiphenyl-4'-yl)-2-(2-trifluoromethoxypyridine-5-yl)ethane
1-[4-(trans-4-ethylcyclohexyl)phenyl]-2-[2-fluoropyridine-5-yl]ethane
1-[4-(trans-4-propylcyclohexyl)phenyl]-2-[2-fluoropyridine-5-yl]ethane
1-[4-(trans-4-butylcyclohexyl)phenyl]-2-[2-fluoropyridine-5-yl]ethane
1-[4-(trans-4-pentylcyclohexyl)phenyl]-2-2-fluoropyridine-5-yl]ethane
1-[4-(trans-4-octylcyclohexyl)phenyl]-2-[2-fluoropyridine-5-yl]ethane
1-[trans-4-(4-ethylphenyl)cyclohexyl]-2-(2-chloropyridine-5-yl)ethane
1-[trans-4-(4-propylphenyl)cyclohexyl]-2-(2-chloropyridine-5-yl)ethane
1-[trans-4-(4-butylphenyl)cyclohexyl]-2-(2-chloropyridine-5-yl)ethane
1-[trans-4-(4-pentylphenyl)cyclohexyl]-2-(2-chloropyridine-5-yl)ethane
1-[trans-4-(4-ethoxyphenyl)cyclohexyl]-2-(2-fluoropyridine-5-yl)ethane
1-[trans-4-(4-propoxyphenyl)cyclohexyl]-2-(2-fluoropyridine-5-yl)ethane
1-trans-4-(4-butoxyphenyl)cyclohexyl]-2-(2-fluoropyridine-5-yl)ethane
1-[trans-4-(4-pentyloxyphenyl)cyclohexyl]-2-(2-fluoropyridine-5-yl)ethane
1-(trans-4-ethylcyclohexyl)-2-(2-fluoropyridine-5-yl)ethane
1-(trans-4-propylcyclohexyl)-2-(2-fluoropyridine-5-yl)ethane
1-(trans-4-butylcyclohexyl)-2-(2-fluoropyridine-5-yl)ethane
1-(trans-4-pentylcyclohexyl)-2-(2-fluoropyridine-5-yl)ethane
1-[trans-4-(trans-4-ethylcyclohexyl)cyclohexyl-2-(2-trifluoromethylpyridine-5-yl)ethane
1-[trans-4-(trans-4-propylcyclohexyl)cyclohexyl]-2-(2-trifluoromethylpyridine-5-yl)ethane
1-[trans-4-(trans-4-butylcyclohexyl)cyclohexyl]-2-(2-trifluoromethylpyridine-5-yl)ethane
1-[trans-4-(trans-4-pentylcyclohexyl)cyclohexyl]-2-(2-trifluoromethylpyridine-5-yl)ethane
1-[trans-4-(trans-4-heptylcyclohexyl)cyclohexyl]-2-(2-trifluoromethylpyridine-5-yl)ethane
1-[trans-4-(trans-4-ethylcyclohexyl)cyclohexyl]-2-(2-fluoropyridine-5-yl)ethane
1-[trans-4-(trans-4-propylcyclohexyl)cyclohexyl]-2-(2-fluoropyridine-5-yl)ethane
1-[trans-4-(trans-4-butylcyclohexyl)cyclohexyl]-2-(2-fluoropyridine-5-yl)ethane
1-[trans-4-(trans-4-pentylcyclohexyl)cyclohexyl]-2-(2-fluoropyridine-5-yl)ethane
1-(trans-4-ethylcyclohexyl)-2-[4-(2-chloropyridin-5-yl)phenyl]-ethane
1-(trans-4-propylcyclohexyl)-2-[4-(2-chloropyridin-5-yl)phenyl-ethane C 124 N 159 I phenyl]-ethane
1-(trans-4-pentylcyclohexyl)-2-4-(2-chloropyridin-5-yl)phenyl]-ethane
1-(trans-4-hexylcyclohexyl)-2-[4-(2-chloropyridin-5-yl)phenyl]-ethane
1-(trans-4-heptylcyclohexyl)-2-4-(2-chloropyridin-5-yl)phenyl]-ethane Example 8

A suspension of 0,02 M of trans-4-(trans-4-ethylcyclohexyl)cyclohexylbromide, 0,04 M of lithium and 0,01 M of $ZnBr_2$ is stirred for 2 hours at about 10° with ultrasonic. 0,02 M of 3-bromo-2,6-difluoropyridine and 0,1 g of $Pd(Ph_3P)_4$ are added and the mixture is stirred for 4 hours.

After customary work-up 2,6-difluoro-3-[trans-4-(trans-4-ethylcyclohexyl)cyclohexyl]pyridine is obtained The following compounds are obtained analogously:
2,6-difluoro-3-trans-4-(trans-4-methylcyclohexyl)cyclohexyl]pyridine
2,6-difluoro-3-[trans-4-(trans-4-propylcyclohexyl)cyclohexyl]pyridine
2,6-difluoro-3-[trans-4-(trans-4-butylcyclohexyl)cyclohexyl]pyridine
2,6-difluoro-3-[trans-4-(trans-4-pentylcyclohexyl)cyclohexyl]pyridine
6-chloro-2-fluoro-3-trans-4-(trans-4-ethylcyclohexyl)cyclohexyl]pyridine
6-chloro-2-fluoro-3-trans-4-(trans-4-propylcyclohexyl)cyclohexyl]pyridine
6-chloro-2-fluoro-3-[trans-4-(trans-4-butylcyclohexyl)cyclohexyl]pyridine
6-chloro-2-fluoro-3-[trans-4-(trans-4-pentylcyclohexyl)cyclohexyl]pyridine
6-chloro-3-[trans-4-(trans-4-ethylcyclohexyl)-cyclohexyl]pyridine
6-chloro-3-[trans-4-(trans-4-propylcyclohexyl)cyclohexyl]pyridine
6-chloro-3-[trans-4-(trans-4-butylcyclohexyl)-cyclohexyl]pyridine 6-chloro-3-[trans-4-(trans-4-pentylcyclohexyl)-cyclohexyl]pyridine
6-chloro-3-[trans-4-(trans-4-heptylcyclohexyl)-cyclohexyl]pyridine
6-trifluoromethyl-3-[trans-4-(trans-4-ethylcyclohexyl)-cyclohexyl]pyridine
6-trifluoromethyl-3-trans-4-(trans-4-propylcyclohexyl)-cyclohexyl]pyridine
6-trifluoromethyl-3-[trans-4-(trans-4-butylcyclohexyl)-cyclohexyl]pyridine
6-trifluoromethyl-3-trans-4-(trans-4-pentylcyclohexyl)-cyclohexyl]pyridine
6-trifluoromethyl-3-trans-4-(trans-4-hexylcyclohexyl)-cyclohexyl]pyridine
6-trifluoromethyl-3-[trans-4-(trans-4-heptylcyclohexyl)-cyclohexyl]pyridine
6-trifluoromethoxy-3-[trans-4-(trans-4-ethylcyclohexyl)cyclohexyl]pyridine
6-trifluoromethoxy-3-[trans-4-(trans-4-propylcyclohexyl)cyclohexyl]pyridine
6-trifluoromethoxy-3-[trans-4-(trans-4-butylcyclohexyl)cyclohexyl]pyridine
6-trifluoromethoxy-3-[trans-4-(trans-4-pentylcyclohexyl)cyclohexyl]pyridine
6-difluoromethoxy-3-[trans-4-(trans-4-ethylcyclohexyl)cyclohexyl]pyridine
6-difluoromethoxy-3-[trans-4-(trans-4-propylcyclohexyl)cyclohexyl]pyridine
6-difluoromethoxy-3-[trans-4-(trans-4-butylcyclohexyl)cyclohexyl]pyridine
6-difluoromethoxy-3-[trans-4-(trans-4-pentylcyclohexyl)cyclohexyl]pyridine
2,6-difluoro-3-(trans-4-ethylcyclohexyl)pyridine
2,6-difluoro-3-(trans-4-propylcyclohexyl)pyridine
2,6-difluoro-3-(trans-4-butylcyclohexyl)pyridine
2,6-difluoro-3-(trans-4-pentylcyclohexyl)pyridine
2,6-difluoro-3-[trans-4-(4-ethylphenyl)cyclohexyl]pyridine
2,6-difluoro-3-[trans-4-(4-propylphenyl)cyclohexyl]pyridine
2,6-difluoro-3-[trans-4-(4-butylphenyl)cyclohexyl]pyridine
2,6-difluoro-3-[trans-4-(4-pentylphenyl)cyclohexyl]pyridine
2,6-difluoro-3-[trans-4-(4-ethoxyphenyl)cyclohexyl]pyridine
2,6-difluoro-3-[trans-4-(4-propoxyphenyl)cyclohexyl]pyridine
2,6-difluoro-3-[trans-4-(4-butoxyphenyl)cyclohexyl]pyridine
2,6-difluoro-3-[trans-4-(4-pentyloxyphenyl)cyclohexyl]pyridine
2,6-difluoro-3-[trans-4-(4-octyloxyphenyl)cyclohexyl]pyridine
6-chloro-2-fluoro-3-[trans-4-(4-ethylphenyl)cyclohexyl]pyridine
6-chloro-2-fluoro-3-[trans-4-(4-propylphenyl)cyclohexyl]pyridine
6-chloro-2-fluoro-3-[trans-4-(4-butylphenyl)cyclohexyl]pyridine
6-chloro-2-fluoro-3-[trans-4-(4-pentylphenyl)cyclohexyl]pyridine
2,6-difluoro-3-[trans-4-(2-fluoro-4-ethylphenyl)cyclohexyl]pyridine
2,6-difluoro-3-[trans-4-(2-fluoro-4-propylphenyl)cyclohexyl]pyridine
2,6-difluoro-3-[trans-4-(2-fluoro-4-butylphenyl)cyclohexyl]pyridine
2,6-difluoro-3-[trans-4-(2-fluoro-4-pentylphenyl)cyclohexyl]pyridine Example 9

Analogously to example 8 2-fluoro-5-[trans-4-(trans-4-ethylcyclohexyl)cyclohexyl]pyridine is obtained by reacting trans-4-(trans-4-ethylcyclohexyl)cyclohexyl-bromide with 2-fluoro-5-bromopyridine.

The following compounds are obtained analogously:
2-fluoro-5-[trans-4-(trans-4-propylcyclohexyl)cyclohexyl]pyridine
2-fluoro-5-[trans-4-(trans-4-butylcyclohexyl)cyclohexyl]pyridine
2-fluoro-5-[trans-4-(trans-4-pentylcyclohexyl)cyclohexyl]pyridine
2-fluoro-5-[trans-4-(trans-4-octylcyclohexyl)cyclohexyl]pyridine
2-chloro-5-[trans-4-(trans-4-ethylcyclohexyl)cyclohexyl]pyridine
2-chloro-5-[trans-4-(trans-4-propylcyclohexyl)cyclohexyl]pyridine
2-chloro-5-[trans-4-(trans-4-butylcyclohexyl)cyclohexyl]pyridine
2-chloro-5-[trans-4-(trans-4-pentylcyclohexyl)cyclohexyl]pyridine
2-trifluoromethyl-5-(trans-4-ethylcyclohexyl)-pyridine
2-trifluoromethyl-5-(trans-4-propylcyclohexyl)-pyridine
2-trifluoromethyl-5-(trans-4-butylcyclohexyl)-pyridine
2-trifluoromethyl-5-(trans-4-pentylcyclohexyl)-pyridine
2-trifluoromethoxy-5-(trans-4-ethylcyclohexyl)-pyridine
2-trifluoromethoxy-5-(trans-4-propylcyclohexyl)-pyridine
2-trifluoromethoxy-5-(trans-4-butylcyclohexyl)-pyridine
2-trifluoromethoxy-5-(trans-4-pentylcyclohexyl)-pyridine
2-difluoromethoxy-5-(trans-4-ethylcyclohexyl)-pyridine
2-difluoromethoxy-5-(trans-4-propylcyclohexyl)-pyridine
2-difluoromethoxy-5-(trans-4-butylcyclohexyl)-pyridine
2-difluoromethoxy-5-(trans-4-pentylcyclohexyl)-pyridine
2-fluoro-5-(trans-4-ethylcyclohexyl)-pyridine
2-fluoro-5-(trans-4-propylcyclohexyl)-pyridine
2-fluoro-5-(trans-4-butylcyclohexyl)-pyridine
2-fluoro-5-(trans-4-pentylcyclohexyl)-pyridine
2-fluoro-5-(trans-4-hexylcyclohexyl)-pyridine
2-fluoro-5-[trans-4-(4-ethylphenyl)cyclohexyl]pyridine
2-fluoro-5-[trans-4-(4-propylphenyl)cyclohexyl]pyridine
2-fluoro-5-[trans-4-(4-butylphenyl)cyclohexyl]pyridine
2-fluoro-5-[trans-4-(4-pentylphenyl)cyclohexyl]pyridine
2-fluoro-5-[trans-4-(4-ethoxyphenyl)cyclohexyl]pyridine
2-fluoro-5-[trans-4-(4-propoxyphenyl)cyclohexyl]pyridine
2-fluoro-5-[trans-4-(4-butoxyphenyl)cyclohexyl]pyridine
2-fluoro-5-[trans-4-(4-pentyloxyphenyl)cyclohexyl]pyridine
2-chloro-5-[trans-4-(4-ethylphenyl)cyclohexyl]pyridine 2-chloro-5-[trans-4-(4-propylphenyl)cyclohexyl]pyridine 2-chloro-5-[trans-4-(4-butylphenyl)cyclohexyl]pyridine 2-chloro-5-[trans-4-(4-pentylphenyl)cyclohexyl]pyridine 2-trifluoromethyl-5-[trans-4-(4-ethylphenyl)cyclohexyl]pyridine 2-trifluoromethyl-5-[trans-4-(4-propylphenyl)cyclohexyl]pyridine 2-trifluoromethyl-5-[trans-4-(4-butylphenyl)cyclohexyl]pyridine 2-trifluoromethyl-5-[trans-4-(4-pentylphenyl)cyclohexyl]pyridine Example 10

A liquid crystalline medium consisting of a) 90% of a mixture A consisting of

24% p-(trans-4-propylcyclohexyl)benzonitrile,

36% p-(trans-4-pentylcyclohexyl)benzonitrile,

25% p-(trans-4-heptylcyclohexyl)benzonitrile and 15% 4-cyano-4'-(trans-4-pentylcyclohexyl)-biphenyl and b) 10% 2,6-difluoro-3-[4-(trans-4-pentylcyclohexyl)-phenylpyridine has a clearing point of 71.2°.

Example 11

A liquid crystalline medium consisting of a) 90% of a mixture A consisting of

22% p-(trans-propylcyclohexyl)-ethylbenzene,

20% p-(trans-propylcyclohexyl)-methoxybenzene,

15% p-(trans-propylcyclohexyl)-ethoxybenzene,

19% 4'-(trans-propylcyclohexyl)-4-ethylbiphenyl

14% 4'-(trans-pentylcyclohexyl)-4-ethylbiphenyl

5% bis-4,4'-(trans-propylcyclohexyl)biphenyl

5% 4'-(trans-4-propylcyclohexyl)-4-(trans-4-pentylcyclohexyl)-biphenyl and b) 10% of 1-(trans-4-propylcyclohexyl)-2-[4-(2-chloropyridin-5-yl)-phenyl]-ethane a clearing point of 77.1 ° C.

What is claimed is:

1. Pyridine derivatives of the formula I

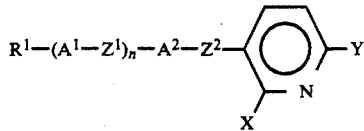

wherein $R^1$ denotes alkyl with up to 12 carbon atoms wherein one or two non-adjacent $CH_2$-groups may also be replaced by —O—, —O—CO—, —CO—O— and/or —CH=CH—, Y is F, Cl, —$CF_3$, —$OCF_3$ or $OCHF_2$, $A^1$ and $A^2$ in each case independently of one another are trans-1,4-cyclohexylene, wherein one or two non-adjacent $CH_2$-groups may also be replaced by —O— or —S—, or 1,4-phenylene which is unsubstituted or substituted by one or more halogen atoms and/or nitrile and/or $CH_3$ groups, and wherein one or more CH groups may also be replaced by N, $Z^1$ and $Z^2$ in each case independently of one another are —CH —CO—O—, —O—CO—, —$CH_2$O—, —$OCH_2$—, —C≡C— or a single bond, X is H, or in case of Y=F or Cl, also F and n is 0, 1 or 2.

2. Pyridine derivatives of claim 1, wherein X is H.

3. Pyridine derivatives of claim 1, wherein X is F.

4. Pyridine derivatives of claim 1 wherein Y is F or Cl.

5. Pyridine derivatives of claim 1 or 3 wherein Y is F or Cl.

6. Pyridine derivatives of claim 1 wherein Y is —$OCF_3$.

7. Pyridine derivatives of claim 1 wherein Y is —$CF_3$.

8. Pyridine derivatives of claim 1 wherein Y is —$OCHF_2$.

9. Pyridine derivatives of claim 1, wherein $R^1$ denotes an unbranched alkyl radical of 2 to 7 carbon atoms.

10. Pyridine derivatives of claims 1, wherein n is 0 or 1.

11. Pyridine derivatives of claims 1, wherein $Z^1$ and $Z^2$ are each a single bond.

12. Pyridine derivatives of claim 1, wherein $Z^2$ is —CO—O—, —CH or —C≡C—.

13. Liquid crystalline medium being a mixture of at least two compounds, characterized in that at least one compound is a pyridine derivative according to claim 1.

14. Liquid crystal display device, characterized in that it contains a liquid crystalline medium according to claim 13.

15. Electrooptical display device, characterized in that it contains a liquid crystalline medium according to claim 13.

* * * * *

UNITED STATES PATENT AND TRADEMARK OFFICE
CERTIFICATE OF CORRECTION

PATENT NO. : 5,205,962
DATED : April 27, 1993
INVENTOR(S) : David COATES ET AL.

It is certified that error appears in the above-identified patent and that said Letters Patent is hereby corrected as shown below:

Claim 12, CoL. 32, Line 46:

Reads: $-CO-O-$, $-CH$ or $-C=C-$.

Should read: $-CO-O-, -CH_2CH_2-$ or $-C=C-$.

Signed and Sealed this

Fourth Day of January, 1994

Attest:

BRUCE LEHMAN

Attesting Officer

Commissioner of Patents and Trademarks